US012797435B2

(12) United States Patent
Mousset et al.

(10) Patent No.: US 12,797,435 B2
(45) Date of Patent: Nov. 17, 2026

(54) COMPOSITION FOR THE TREATMENT OF EMOTIONAL DISORDERS

(71) Applicant: Pierre-Yves Mousset, Latresne (FR)

(72) Inventors: Pierre-Yves Mousset, Latresne (FR); Daniel Beracochea, Bordeaux (FR); Sophie Lafay, Marolles en Hurepoix (FR)

(73) Assignee: Pierre-Yves Mousset, Latresne (FR)

( * ) Notice: Subject to any disclaimer, the term of this patent is extended or adjusted under 35 U.S.C. 154(b) by 744 days.

(21) Appl. No.: 17/625,355

(22) PCT Filed: Jul. 9, 2020

(86) PCT No.: PCT/FR2020/051231
§ 371 (c)(1),
(2) Date: Jan. 7, 2022

(87) PCT Pub. No.: WO2021/005310
PCT Pub. Date: Jan. 14, 2021

(65) Prior Publication Data

US 2022/0249591 A1 Aug. 11, 2022

(30) Foreign Application Priority Data

Jul. 10, 2019 (FR) ....................................... 1907747

(51) Int. Cl.

| | |
|---|---|
| ***A61P 25/22*** | (2006.01) |
| ***A61K 9/00*** | (2006.01) |
| ***A61K 31/198*** | (2006.01) |
| ***A61K 35/747*** | (2015.01) |
| ***A61K 36/9066*** | (2006.01) |
| ***A61K 45/06*** | (2006.01) |
| ***A61P 25/24*** | (2006.01) |

(52) U.S. Cl.
CPC ............ *A61K 36/9066* (2013.01); *A61K 9/00* (2013.01); *A61K 31/198* (2013.01); *A61K 35/747* (2013.01); *A61K 45/06* (2013.01); *A61P 25/22* (2018.01); *A61P 25/24* (2018.01)

(58) Field of Classification Search
None
See application file for complete search history.

(56) References Cited

U.S. PATENT DOCUMENTS

2021/0398449 A1* 12/2021 Banavar ............... C12Q 1/6869

FOREIGN PATENT DOCUMENTS

| | | |
|---|---|---|
| CN | 107549813 | * 1/2018 |
| CN | 109527273 | 3/2019 |
| JP | 2016199491 | 12/2016 |
| KR | 20090083149 | 8/2009 |
| KR | 20110117591 | 10/2011 |
| WO | WO 2011/132831 | 10/2011 |
| WO | WO 2013/004740 | 1/2013 |
| WO | WO 2018/220429 | 12/2018 |

OTHER PUBLICATIONS

Mutagenics Clinical Detoxification Program Guide; published on line on May 15, 2017 https://metagenicsinstitute.co.nz>detox, retrieved Jun. 4, 2024; pp. 1-16.*
Yadav et al. "Effect of Cyclodextrin Complexation of Curcumin on its Solubility and Antiangiogenic and Anti-inflammatory Activity in Rat Colitis Mode" AAPS PharmSciTech., 2009, vol. 10, No. 3, pp. 752-762.*
Azhari et al. Earth and Environmental Science, 2018, 205, 012048, pp. 1-8.*
Anonymous: "Products: Glutamine Forte Powder—The Way Up" Jun. 20, 2019, XP055677691, obtained from the internet: URL:https://web.archive.org/web/20190620231717/http://www.thewayup.com/products/0178.cfm, obtained on Mar. 19, 2020, pp. 1-2.
Anonymous: "Optimized Superfood Meal Replacement Record ID 10237526" GNPD, Oct. 1, 2005, pp. 1-4, XP055224685, obtained from the internet: URL:http://www.gnpd.com/sinatra/recordpage/10237526/from search/Ghs8ileYGW/, obtained on Oct. 30, 2015.
Kulkarni, SK et al. "An overview of curcumin in neurological disorders" *Indian Journal of Pharmaceutical Sciences*, 2010, pp. 1-6, vol. 72, Issue 2.
Ng, Q.X. et al. "Clinical Use of Curcumin in Depression: A Meta-Analysis" *Journal of the American Medical Directors Association*, 2017, pp. 503-508, vol. 18.
Written Opinion in International Application No. PCT/FR2020/051231, Sep. 14, 2020, pp. 1-13.
Dai, C et al. "The Natural Product Curcumin as an Antibacterial Agent: Current Achievements and Problems" *Antioxidants*, Feb. 25, 2022, pp. 1-21, vol. 11, No. 459.

* cited by examiner

*Primary Examiner* — Vera Afremova
(74) *Attorney, Agent, or Firm* — Greer, Burns & Crain, Ltd.

(57) ABSTRACT

The present invention relates to a composition comprising glutamine, curcuma extract and *Lactobacillus rhamnosus* and its use in human nutrition or for the treatment or prevention of anxiety disorders and/or mood disorders, in particular depression.

13 Claims, 5 Drawing Sheets

COMPOSITION FOR THE TREATMENT OF EMOTIONAL DISORDERS

CROSS-REFERENCE TO RELATED APPLICATION

This application is the U.S. national stage application of International Patent Application No. PCT/FR2020/051231, filed Jul. 9, 2020.

TECHNICAL FIELD

The present invention relates to the health field and more particularly concerns a composition for preventing and/or treating anxiety disorders and/or mood disorders, in particular depression.

TECHNOLOGICAL BACKGROUND

Psychiatric disorders are considered to be the main health challenge of the 21st century on account of their high prevalence, 38% of the population of Europe, and of the enormous handicap associated therewith. Major depressive disorders (MDD) are the most common, with a prevalence of 16% in the course of a lifetime. These recurrent chronic disorders have major psychosocial consequences and considerable costs for the community. The projections indicate that MDDs will be the second contributor to care costs in 2020, before occupying first place in 2030.

For decades, the main theory of the physiopathology of depression has been that it is the result of the underactivity of the monoamine neuromediators, in particular serotonin and noradrenaline. At the present time, more than two-thirds of patients treated with an antidepressant of the selective serotonin reuptake inhibitor (SSRI) class prescribed as a first line treatment do not show any remission. Furthermore, 20% to 30% of patients withstand all the medication strategies.

In the course of the last decade, the understanding of the physiopathology of depression has greatly evolved with the contribution of novel technologies. Thus, cerebral imaging has shown that depression is associated with a loss of "white matter" notably concerning the medial prefrontal cortex which is involved in regulating the emotions. Now, the astrocytes which reside therein are key elements in neuromediator regulation, which do not belong to the monoamine family but to the glutamine-glutamate-GABA cycle.

Moreover, numerous studies also show substantial biological alterations associated with depression, notably an immuno-inflammatory syndrome, alterations of the corticotropic axis, which is the main neuroendocrine axis of response to stress, metabolic abnormalities, and oxidative stress. Recent data, arising mainly from animal studies, indicate that these pathways, which are poorly regulated in the case of depression, are modulated by the intestinal microbiota.

The intestinal microbiota, which is described as "an additional organ" and is composed of more than 1000 different identified bacterial species, may also play a beneficial role for the host by exerting numerous biological functions, such as aiding digestion, the absorption of nutrients and the metabolization of substrates, combating pathogens, maintaining the integrity of the intestinal epithelium, or establishing and managing the homeostasis of immune responses.

Studies using different but complementary approaches, such as rodents born and raised germ-free, antibiotics, probiotics, studies on gastrointestinal infections and on the transplantation of fecal microbiota, have shown that the intestinal microbiota also contributes toward regulating the central nervous system. This interaction is termed a "gut-brain axis" interaction, defined as a bidirectional communication system between the central nervous system and the digestive apparatus notably via neuronal, neuroimmune and neuroendocrine pathways. From a clinical viewpoint, digestive symptoms are very frequently associated with psychiatric disorders. Thus, 60% to 85% of patients suffering from irritable bowel syndrome have psychiatric symptoms, of which 20% to 40% present with a clinical depression, which is generally more severe than for the normal population.

The discovery of the mechanisms via which the commensal bacteria are involved in the functioning of the brain thus opens the way to the development of novel therapeutic perspectives based on the microbiota, for caring for mixed anxiety-depressive disorders.

Despite the progress made in the understanding of mixed anxiety-depressive disorders, the need for alternatives to the currently-available drug treatments remains at the forefront.

SUMMARY OF THE INVENTION

The inventors have shown that, surprisingly, there is synergism of action between glutamine, a curcuma extract and *Lactobacillus rhamnosus* for the regulation of anxiety and depression symptoms, thus resulting in an improvement comparable to that obtained with a reference antidepressant drug in this field (clomipramine). This combination significantly reduces anxiety and depression disorders.

The invention relates to a pharmaceutical, nutraceutical or food composition comprising glutamine, a curcuma extract and *Lactobacillus rhamnosus* in the following proportions:

from 70% to 97% by weight of glutamine, from 1% to 15% by weight of curcuma extract, from 0.02% to 5% by weight of *Lactobacillus rhamnosus*, per 100% by weight of the sum of glutamine, curcuma extract and *Lactobacillus rhamnosus*.

Preferably, the composition comprises from 70% to 97% by weight of glutamine, from 1% to 15% by weight of curcuma extract and from 0.02% to 5% by weight of *Lactobacillus rhamnosus*, per 100% by weight of the pharmaceutical, nutraceutical or food composition.

In a particular aspect, the composition comprises from 85% to 95% by weight of glutamine, from 3% to 10% by weight of curcuma extract and from 0.25% to 5% by weight of *Lactobacillus rhamnosus*, per 100% by weight of the sum of glutamine, curcuma extract and *Lactobacillus rhamnosus*.

In a particular aspect, the curcuma extract comprises at least 10% of curcuminoids.

In a particular aspect, the curcuma extract also comprises a cyclodextrin, in particular a $\gamma$-cyclodextrin.

In particular, the *Lactobacillus rhamnosus* strain used in the composition is the strain *Lactobacillus rhamnosus* GG.

Preferably, the *Lactobacillus rhamnosus* bacteria are in live form.

The composition according to the invention may also comprise: one or more prebiotics; and/or vitamins, minerals and/or trace elements; and/or powders or extracts of plants, fruit, vegetables, algae or fungi; and/or one or more probiotic microorganisms chosen from the group consisting of bacteria of the genus *Bacillus, Bacteroides, Enterobacteriaceae, Enterococcus, Faecalibacterium, Fusobacterium, Lactobacillus, Odoribacter, Parabacteroides, Pediococcus, Roseburia, Ruminococcus* and *Streptococcus* and/or yeasts, in particular of the genus *Saccharomyces*.

The invention also relates to a composition according to the invention for its use as a food supplement or medicament, in particular for human or veterinary use; or for its use in preventing or treating an emotional disorder in an individual.

In particular, the disorder from which the individual is suffering is an anxiety disorder and/or a mood disorder, in particular depression or anxiety.

Preferably, the composition according to the invention is in a form intended to be administered enterally, preferably orally.

In particular, the composition is in a form intended to be administered such that the daily dose of the composition is between 0.5 and 10 g, preferably between 1 and 5 g.

According to one embodiment, the composition is in a form intended to be administered such that the daily dose of glutamine is between 0.5 and 10 g, the daily dose of curcuma extract is between 25 mg and 500 mg and the daily dose of *Lactobacillus rhamnosus* is between 0.05 mg and 500 mg or between $1\times10^7$ CFU and $1\times10^{11}$ CFU.

In a particular aspect, said composition is in the form of dose units, for example in the form of tablets or gel capsules, each dose unit comprising:

- from 0.5 g to 10 g of glutamine,
- from 25 mg to 500 mg of curcuma extract, and
- from 0.05 mg to 500 mg or between $1\times10^7$ CFU and $1\times10^{11}$ CFU of *Lactobacillus rhamnosus.*

In another particular aspect, each dose unit comprises:

- from 0.5 g to 2 g of glutamine,
- from 50 mg to 100 mg of curcuma extract, and
- from 10 mg to 20 mg of *Lactobacillus rhamnosus.*

Finally, the invention relates to a pharmaceutical, nutraceutical or food kit comprising the composition according to the invention, in which the composition is in the form of separate compositions, comprising:

- a first composition comprising the bacterium *Lactobacillus rhamnosus*, for example combined with one or more excipients, and
- a second composition comprising glutamine and the curcuma extract, for example combined with one or more excipients.

Finally, the invention relates to a pharmaceutical, nutraceutical or food kit according to the invention for its use as a food supplement or medicament, in particular for human or veterinary use; or for its use in preventing or treating an emotional disorder in an individual.

Preferably, the emotional disorder is an anxiety disorder and/or a mood disorder, in particular depression or anxiety.

DETAILED DESCRIPTION OF THE INVENTION

Introduction

Figure 1:
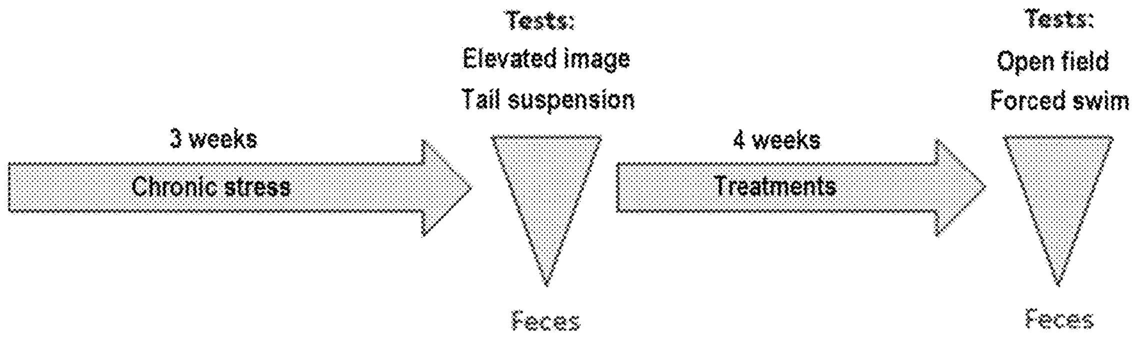
FIG. 1 represents the running scheme of the in vivo study.

The invention relates to a composition comprising a curcuma extract, glutamine and a bacterial strain *Lactobacillus rhamnosus*, in which the composition comprises particular proportions of these three ingredients, preferably from 50% to 95% by weight of glutamine, from 1% to 15% by weight of curcuma extract and from 0.02% to 5% by weight of *Lactobacillus rhamnosus*, per 100% of the composition. This composition is notably a pharmaceutical composition, for example for the preparation of drugs, or a nutraceutical composition, for example for the preparation of food supplements, or a food composition for the preparation of foods, functional foods or foods for specific groups.

The invention also relates to the use of this composition for preventing or treating anxiety disorders and/or mood disorders, in particular depression, in an individual.

The inventors have in fact shown, surprisingly, that there is synergism of action between these three ingredients in terms of regulation of the anxiety and depression symptoms, resulting in an improvement in the mental well-being that is much greater than the expected effect.

The inventors have particularly shown:

- that the combination of glutamine and of *Lactobacillus rhamnosus* makes it possible to reduce anxiety and depressive disorders in an equivalent manner to that of glutamine or *Lactobacillus* alone;
- that the combination of glutamine or of *Lactobacillus* with a curcuma extract has a tendency to reduce the effects of glutamine or of the *Lactobacillus* alone;
- that the combination of glutamine, *Lactobacillus rhamnosus* and a curcuma extract makes it possible to very significantly reduce anxiety and depressive disorders when compared with the ingredients tested separately or with the ingredients mixed in pairs;

that the combination of glutamine, the bacterium *Lactobacillus rhamnosus* and a curcuma extract makes it possible, surprisingly, to obtain results comparable to those obtained with a reference drug for the treatment of depression (clomipramine).

The inventors thus describe for the first time the advantage of a composition based on glutamine, a curcuma extract and *Lactobacillus rhamnosus* in the field of psychiatry, and also its capacity for regulating the mood or the emotional state of an individual, notably by reducing anxiety and/or depression in an individual, and also the symptoms associated therewith. This composition may thus be advantageously administered to individuals presenting a risk or being at risk of developing anxiety and/or depressive states, in particular anxiety and depression symptoms.

Definitions

As used herein, the terms "disorder", "abnormality" or "disturbance" are interchangeable and refer to an organ, a part, a structure or a system of the body which functions incorrectly. Preferably, the term "disorder" denotes a health disorder, for example a disorder which disrupts the normal physical or mental functions. Preferably, the disorder is an anxiety disorder and/or a mood disorder, in particular depression or an isolated anxiety symptomatology and/or depressive episode.

As used herein, the terms "anxiety disorders", "anxiety" and "anxiogenic symptom" are interchangeable and represent a category of mental disorders characterized by negative feelings, in particular worry and/or nervousness regarding coming events and/or fear and/or nervousness in reaction to events under way. Anxiety may be characterized by a distressing emotional state characterized by a "groundless" fear, a feeling of anxious expectation, and neuro-vegetative manifestations often in the foreground, such as palpitations, tightness of the chest, uneasy breathing, a "lump in the throat", etc. Anxiety disorders include, without being limited to, generalized anxiety disorders, phobia, panic, hypochondria, obsessive-compulsive disorder, stress, post-traumatic stress, social anxiety, separation anxiety, end-of-life anxiety and situational anxiety.

The terms "mood disorder", "thymic disorders" and "affective disorders" refer herein to a condition characterized by a disturbance in an individual's emotional or behavioral regulation, which reflects dysfunction of the psychological, biological, and/or developmental processes underlying the mental function. In particular, these terms refer to a negative alteration of an individual's mood or emotional state. Mood disorders include, without being limited to, depressive disorders, bipolar disorders, dysthymia, seasonal affective disorder (SAD), or a mixed anxiety-depressive disorder.

"Depressive disorder", "depressive symptoms" or "depression" are understood herein as meaning a negative alteration in an individual's mood, in particular a low mood, lack of interest, psychomotor slowness or agitation, appetite changes, lack of concentration, indecisiveness, or other depression-related cognitive symptoms, such as excessive guilt or feelings of uselessness, lack of energy or fatigue, possibly leading to suicidal thoughts. A "depressive symptom" thus comprises any feeling of sadness and lack of interest, and is typically based on an imbalance in one or more neurotransmitters. Depressive disorders include, without being limited to, depression, major depression, melancholic depression, postpartum depression and atypical depression.

As used herein, the term "well-being" denotes a positive state of health or of comfort, for example relative to a reference population or to a previous state. As used herein, the term "mental well-being" refers to a positive mental state, relative to a reference population or to a previous emotional state. For example, in a depressed individual with low self-esteem or anxiety, mental well-being may show improvement in response to a treatment directed toward improving the mood, self-esteem or anxiety. The "mental well-being" may be accompanied by "physical well-being" which refers to one or more positive aspects of an individual's physical state of health and comprises, for example, relief of the somatic symptoms associated with a mood disorder, in particular depression or anxiety.

The term "treatment" refers herein to the generation of a desired pharmacological, mental and/or physiological effect. The effect may be prophylactic in terms of total or partial prevention of a disorder or symptom and/or may be therapeutic in terms of partial or total curing of a disorder and/or of an attributable adverse effect thereof. As used herein, the term "treatment" means any treatment of a disease or disorder in a mammal, in particular a human, for: reducing the incidence and/or risk of relapse of the disease or disorder over a symptom-free period; relieving or reducing a symptom of the disease or disorder; preventing the disease or disorder from occurring or recurring in an individual who may be predisposed to the disease but who has not yet been diagnosed as having it; inhibiting the disease or disorder, i.e., halting its development (e.g., reducing the rate of progression); reducing the frequency of episodes of the disease or disorder; and alleviating the disease or disorder, i.e., bringing about a total or partial regression of the disease or disorder.

The terms "individual", "host", "subject" and "patient" are used interchangeably herein and denote a mammal, more particularly an animal subject and even more particularly a human. When it concerns an animal, the animal may be a pet such as a cat or a dog, or a reared animal such as a horse.

As used herein, a "pharmaceutical composition" denotes a preparation of one or more of the active agents with other optional chemical components such as physiologically suitable supports and/or excipients. The purpose of a pharmaceutical composition is to facilitate the administration of the active agent to an organism. The compositions of the present invention may be in a form that is suitable for any conventional route of administration or use. The pharmaceutical composition according to the invention covers pharmaceutical compositions used in human medicine and pharmaceutical compositions used in animal medicine, i.e. veterinary compositions. Preferably, the pharmaceutical composition also comprises a pharmaceutically acceptable vehicle.

As used herein, the terms "pharmaceutically acceptable support" or "pharmaceutically acceptable excipient" or "pharmaceutically acceptable vehicle" are interchangeable and comprise any compound or combinations of compounds that are known to a person skilled in the art as being useful in the formulation of pharmaceutical or veterinary compositions. In the context of the present invention, the term "physiologically acceptable" or "pharmaceutically acceptable" refers to any medium or additive which does not interfere with the efficacy of the biological activity of the active principle (in this instance, the combination of glutamine, curcuma extract and *L. rhamnosus*), which is not excessively toxic to the individual at the concentrations at which it is administered and/or which does not produce an adverse reaction when it is administered to a human or an animal. A physiologically acceptable vehicle, support or excipient may be suitable for administration to humans and/or animals (in particular to mammals).

The term "drug" as used herein encompasses drugs for human and animal use in human and veterinary medicine and refers to any pharmacologically acceptable substance which affords a therapeutic and/or beneficial effect. The term "drug" as used herein is not necessarily limited to substances requiring a marketing authorization, but may comprise substances that may be used in cosmetics and natural remedies.

The term "nutraceutical" refers to a composition or product manufactured from food substances, but made available in the form of a tablet, powder, potion or other presentation forms not usually associated with food, and having a beneficial or protective physiological effect against animal or human disorders or diseases. Notably included in this definition are food supplements, certain foods for specific groups or meal replacements.

The term "food supplement" means herein any composition which is formulated and administered separately from other foods and has the purpose of supplementing an individual's nutritional intake, having a pharmacologically acceptable form, notably in the form of hard gel capsules, tablets, soft capsules, sachets, stick-packs, syrups, droppers, or any other suitable form that is well known to a person skilled in the art.

The terms "food", "food product" and "foodstuff" are used interchangeably herein and comprise, in addition to foods commonly consumed by humans and animals such as pets or livestock, functional foods and foods for specific groups, which themselves comprise foods intended for special medical purposes.

The term "functional food" refers herein to a conventional food which forms part of the normal diet and affords physiological benefits and/or reduces the risk of diseases or disorders and/or reduces the symptoms associated therewith, beyond the traditional nutrients it contains.

As used herein, the term "food additive" refers to a composition which is intended to be mixed with one or more other foods before being administered to an individual. More particularly, the term "food additive" means any additive as defined by the Codex *Alimentarius*, General Standard for Food Additives—Codex Stan 192-1995, i.e., any substance which is not consumed alone as a foodstuff, nor used alone as a characteristic ingredient of a foodstuff, whether or not it has nutritional value, and for which the deliberate addition to a foodstuff for a technological (including organoleptic) purpose at any step in the manufacture, processing, preparation, treatment, packaging, wrapping, transportation or storage of said foodstuff brings about, or may reasonably be expected to bring about, directly or indirectly, its incorporation or the incorporation of its derivatives into that foodstuff or affect the particular features of said foodstuff in some other way.

As used herein, a "prebiotic" refers to an ingredient or substrate which, when used selectively by a host microorganism, imparts a health benefit. It may enable beneficial changes to be induced both in the composition and/or in the activity of a probiotic. A prebiotic may be an edible food or beverage or an ingredient thereof. Prebiotics may include complex carbohydrates, polyphenols and polyunsaturated fatty acids. A prebiotic is typically an indigestible carbohydrate such as an oligo- or polysaccharide, or a sugar alcohol, which is not degraded or absorbed in the upper digestive tract in the absence of gut microorganisms. Preferably, the prebiotics according to the invention are as defined in the Order of Sep. 26, 2016 establishing the list of substances for nutritional or physiological purposes permitted in food supplements and the conditions for using same.

As used herein, the term "probiotic" refers to live or inactivated bacteria, which, when administered in adequate amounts, have a beneficial effect on the host organism. These compositions are advantageous in that they are suitable for administration to humans and to other mammalian subjects. The probiotic substances contain a number of probiotic microorganisms that is high enough to exert a direct or indirect action on the gut microbiota. It should be noted that, for the purposes of the present description, the term "probiotic" means any biologically active form of probiotic, preferably but not limited to lactobacilli, bifidobacteria, *bacillus*, streptococci, enterococci, propionibacteria or saccharomycetes, but also other microorganisms constituting the "normal gut flora", or fragments of the bacterial wall or of the DNA of these microorganisms. Preferably, the probiotics according to the invention are as defined by the Food and Agriculture Organization of the United Nations (FAO) and the World Health Organization (WHO) in the Joint FAO/WHO Expert Consultation on the evaluation of the health and nutritional properties of probiotics in food including milk powder containing live lactic acid bacteria performed in 2001. In a particular aspect, the term "probiotic bacteria" means bacteria of the species *Lactobacillus rhamnosus*, more particularly of the strain *Lactobacillus rhamnosus* GG.

The terms "microbiota" or "microflora" used hereinbelow are interchangeable and denote all microbial species present (sustainably or transiently) in an environment, comprising eukaryotes, archaea, prokaryotes and viruses. The term "microbiome" refers to the "genetic content" of the microbiota and comprises genomic DNA, ribosomal RNA, the epigenome, plasmids, and any other type of genetic information in the microbiota. Preferentially, these terms refer herein to bacteria of the human or animal gut microbiota.

As used herein, the term "bacterium" denotes any prokaryotic microorganism existing in the form of a single cell, in a group or in an aggregate of individual cells. The term "bacterium" encompasses all variants of bacteria (for example endogenous bacteria or environmental bacteria), more particularly the bacteria of the human or animal microbiota, notably the gut microbiota. The bacteria of the present invention belong to the Gram-positive bacterial subdivisions, particularly of the species *Lactobacillus rhamnosus*, preferentially of the GG strain.

As used herein, the term "comprising" or "comprises" is used in reference to substances, compounds or processes which are essential to the invention, but which are open to the inclusion of nonspecific elements, which may or may not be essential. The use of "comprising" indicates inclusion rather than limitation.

The term "and/or" as used herein should be considered as being a specific description of each of the two specified features or components, with or without the other. For example, "A and/or B" should be considered as being a specific disclosure of each of the following elements: (i) A, (ii) B and (iii) A and B, as if each were presented individually.

The term "about" as used herein in relation with all the values (including the lower and upper ends of numerical ranges) means any value having an acceptable variation t ranging up to ±10% (for example±0.5%, ±1%, ±1.5%, ±2%, ±2.5%, ±3%, ±3.5%, ±4%, ±4.5%, ±5%, ±5.5%, ±6%, ±6.5%, ±7%, ±7.5%, ±8%, ±8.5%, ±9%, ±9.5%). The use of the word "about" at the start of a list of values modifies each of them (i.e., "about 1, 2 and 3" refers to about 1, about 2 and about 3). In addition, when a list of values is described (e.g., about 50%, 60%, 70%, 80%, 85%, or 86%), the list includes all its intermediate and fractional values (for example 54% or 85.4%).

The term "consists essentially of" is used herein to define a composition in which elements other than those mentioned represent not more than 10% by weight of the composition, preferably not more than 5% by weight, and more specifically not more than 1% by weight.

Pharmaceutical, Nutraceutical or Food Compositions

A subject of the present invention is a food, nutraceutical, pharmaceutical or veterinary composition comprising or consisting essentially of glutamine, a curcuma extract and a probiotic of the species *Lactobacillus rhamnosus*, preferably in particular proportions, notably between these three ingredients. The combination of these three ingredients constitutes the active principle of the composition.

According to the invention, the term "combination of active ingredients" or "association of active ingredients" means a combination of active agents which can act cooperatively or synergistically in order to obtain one or more pharmacological and/or physiological and/or nutritional effects directed toward improving the general state of an individual and/or toward treating or preventing a pathology or one of the associated symptoms or disorders thereof. The combination of active ingredients according to the invention particularly finds an application in the care of individuals who are suffering from or who are liable to suffer from one or more emotional disorders.

In a first aspect, the composition comprises glutamine, a curcuma extract and *Lactobacillus rhamnosus*, preferably the strain *Lactobacillus rhamnosus* GG, the glutamine, the curcuma extract and the *Lactobacillus rhamnosus* bacteria being present in the composition in the following proportions:

- from 50% to 95% by weight of glutamine,
- from 1% to 15% by weight of curcuma extract,
- from 0.02% to 5% of *Lactobacillus rhamnosus* probiotic, preferably of the strain *Lactobacillus rhamnosus* GG, per 100% by weight of the sum of glutamine, curcuma extract and *Lactobacillus rhamnosus.*

Preferably, the curcuma extract contains at least 10%, 15% or 20% by weight of curcuminoids. According to a particular embodiment, the curcuma extract is a standardized curcuma extract. In a particular aspect, the curcuma extract is encapsulated and more preferably the curcuma extract is encapsulated with a cyclodextrin, notably γ-cyclodextrin.

In a more particular aspect, the composition comprises or consists essentially of:

- from 50% to 95% by weight of glutamine,
- from 1% to 15% by weight of curcuma extract,
- from 0.02% to 5% by weight of *Lactobacillus rhamnosus* probiotic, preferably of the strain *Lactobacillus rhamnosus* GG, per 100% by weight of the composition.

In another particular aspect, the composition according to the invention may comprise or consist essentially of:

- from 50% to 95% by weight of glutamine,
- from 0.1% to 4.5% by weight of curcuminoids,
- from 0.02% to 5% by weight of *Lactobacillus rhamnosus* probiotic, preferably of the strain *Lactobacillus rhamnosus* GG, per 100% by weight of the sum of glutamine, curcuma extract and *Lactobacillus rhamnosus* or per 100% by weight of the composition.

In another particular aspect, the composition comprises or consists essentially of:

- from 50% to 95% by weight of glutamine,
- from 0.1% to 3.3% by weight of curcumin,
- from 0.02% to 5% by weight of *Lactobacillus rhamnosus* probiotic, preferably of the strain *Lactobacillus rhamnosus* GG, per 100% by weight of the composition or per 100% by weight of the sum of glutamine, curcumin and *Lactobacillus rhamnosus.*

In another particular aspect, the composition comprises or consists essentially of:

- from 70% to 97% by weight of glutamine, preferably 75%, 80%, 85%, 90% to 95%, 96% or 97% by weight of glutamine,
- from 3% to 10%, preferably from 3% to 6% and most preferably from 4% to 5% by weight of curcuma extract,
- from 0.25% to 5%, preferably from 0.3% to 1%, preferentially from 0.3% to 0.6%, most preferably from 0.4% to 0.5% by weight of *Lactobacillus rhamnosus* probiotic, the strain preferably being *Lactobacillus rhamnosus* GG, per 100% by weight of the composition or per 100% by weight of the sum of glutamine, curcumin and *Lactobacillus rhamnosus.*

In another particular aspect, the composition comprises or consists essentially of:

- from 75% to 95% by weight of glutamine, preferably 75%, 80%, 85%, 90% to 95%, 96% or 97% by weight of glutamine,
- from 3% to 10%, preferably from 3% to 6% and most preferably from 4% to 5% by weight of curcuma extract,
- from 0.25% to 5%, preferably from 0.3% to 1%, preferentially from 0.3% to 0.6%, most preferably from 0.4% to 0.5% by weight of *Lactobacillus rhamnosus* probiotic, the strain preferably being *Lactobacillus rhamnosus* GG, per 100% by weight of the composition or per 100% by weight of the sum of glutamine, curcumin and *Lactobacillus rhamnosus.*

In another particular aspect, the composition comprises or consists essentially of:

- from 85% to 97% by weight of glutamine, preferably 85% to 95% by weight of glutamine,
- from 3% to 10%, preferably from 3% to 6% and most preferably from 4% to 5% by weight of curcuma extract,
- from 0.25% to 5%, preferably from 0.3% to 1%, preferentially from 0.3% to 0.6%, most preferably from 0.4% to 0.5% by weight of *Lactobacillus rhamnosus* probiotic, the strain preferably being *Lactobacillus rhamnosus* GG, per 100% by weight of the composition or per 100% by weight of the sum of glutamine, curcumin and *Lactobacillus rhamnosus.*

In another particular aspect, the composition comprises or consists essentially of:

- from 90% to 96% by weight of glutamine, preferably 90% to 95% by weight of glutamine,
- from 3% to 10%, preferably from 3% to 6% and most preferably from 4% to 5% by weight of curcuma extract, from 0.25% to 5%, preferably from 0.3% to 1%, preferentially from 0.3% to 0.6%, most preferably from 0.4% to 0.5% by weight of *Lactobacillus rhamnosus* probiotic, the strain preferably being *Lactobacillus rhamnosus* GG, per 100% by weight of the composition or per 100% by weight of the sum of glutamine, curcumin and *Lactobacillus rhamnosus*.

In another particular aspect, the composition according to the invention may comprise or consist essentially of:

- from 93% to 96% by weight of glutamine, preferably 93% to 95% by weight of glutamine,
- from 3% to 10%, preferably from 3% to 6% and most preferably from 4% to 5% by weight of curcuma extract,
- from 0.25% to 5%, preferably from 0.3% to 1%, preferentially from 0.3% to 0.6%, most preferably from 0.4% to 0.5% by weight of *Lactobacillus rhamnosus* probiotic, the strain preferably being *Lactobacillus rhamnosus* GG, per 100% by weight of the composition or per 100% by weight of the sum of glutamine, curcumin and *Lactobacillus rhamnosus*.

Other examples of proportions will be more particularly described below for each compound. In particular, the composition according to the invention may comprise the various ingredients in the proportions described below in the paragraphs described below, and any combination of these ingredients and of the respective proportions thereof.

Unless otherwise mentioned, the proportions expressed as percentages correspond to mass percentages relative to the total weight of the item under consideration (e.g. the pharmaceutical, nutraceutical or food composition).

The composition may also comprise other compounds or ingredients such as additives or excipients as described below. Preferably, the weight percentage of these ingredients does not exceed 50%, 40%, 30%, 20%, 10% or 5% of the total weight of the composition, i.e. by weight of the combination of the three ingredients glutamine, curcuma extract and *Lactobacillus rhamnosus*, to which are added the other ingredients such as the excipients.

In one embodiment, the ratios of these three active agents (Glutamine/*L. rhamnosus*, Glutamine/*Curcuma* Extract and *Curcuma* Extract/*L. rhamnosus*) are, respectively, between 200 to 1 (200:1), 20 to 1 (20:1) and 10 to 1 (10:1), respectively. Thus, any formulation which contains up to 10 times more curcuma extract than *L. rhamnosus* and/or up to 20 times more glutamine than curcuma extract and/or up to 200 times more glutamine than *L. rhamnosus* would fall within the scope of the present invention.

According to one embodiment, the composition comprises the three ingredients (glutamine, curcuma extract and *Lactobacillus rhamnosus*) in the same composition. Alternatively, these three compounds may be included in compositions intended to be administered separately, for example in two different gel capsules, but still in the proportions as described above.

Glutamine

Glutamine is an amino acid that is considered for regulatory purposes as a nutritional and/or physiological substance. Preferably, the composition according to the invention comprises synthetic glutamine, which is preferably allergen-free, preferentially having the CAS number 56-85-9. In a particular embodiment, the composition according to the invention comprises L-glutamine, preferentially in powder form.

The composition according to the present invention contains from 50% to 95%, from 50% to 90%, from 50% to 85%, from 50% to 80%, from 50% to 75%, from 50% to 70%, from 50% to 65%, from 50% to 60%, from 50% to 55%, from 55% to 95%, from 55% to 90%, from 55% to 85%, from 55% to 80%, from 55% to 75%, from 55% to 70%, from 55% to 65%, from 55% to 60%, from 60% to 95%, from 60% to 90%, from 60% to 85%, from 60% to 80%, from 60% to 75%, from 60% to 70%, from 60% to 65%, from 65% to 95%, from 65% to 90%, from 65% to 85%, from 65% to 80%, from 65% to 75%, from 65% to 70%, from 70% to 95%, from 70% to 90%, from 70% to 85%, from 70% to 80%, from 70% to 75%, from 75% to 95%, from 75% to 90%, from 75% to 85%, from 75% to 80%, from 80% to 95%, from 80% to 90%, from 80% to 85%, 85% to 95%, 85% to 90%, from 90% to 95%, from 90% to 96% or from 90% to 97% of glutamine as defined previously, preferably per 100% by weight of the sum of the three ingredients: glutamine, curcuma extract and *Lactobacillus rhamnosus* or per 100% by weight of the composition. Preferentially, the composition according to the present invention contains from 70% to 95%, from 75% to 95%, from 85% to 95%, from 90% to 95%, from 70% to 96%, from 75% to 96%, from 85% to 96%, from 90% to 96%, from 70% to 97%, from 75% to 97%, from 85% to 97%, from 90% to 97% of glutamine powder per 100% by weight of the three ingredients: glutamine, curcuma extract and *Lactobacillus rhamnosus* or per 100% by weight of the composition.

According to a very particular embodiment, the composition according to the present invention contains between 93% and 96% or between 93% and 95% and most particularly between 94% and 95% of glutamine per 100% by weight of the three ingredients (glutamine, curcuma extract and *Lactobacillus rhamnosus*) or per 100% of the total weight of the composition.

The daily dose of glutamine may be between 0.5 and 10 g.

*Curcuma* Extract

*Curcuma longa* L., also known as curcumin, curcuma or turmeric, is a perennial plant originating from Asia which belongs to the Zingiberaceae family. The curcumin rhizome consists of mucilages, polysaccharides, essential oils, polyphenols and curcuminoids, which notably give the rhizome its yellow/orange color. The term "curcuminoids" means compounds of the diarylheptanoid type notably comprising curcumin (CAS number 458-37-7) and derivatives thereof such as demethoxycurcumin (CAS number 22608-11-3) or bis-demethoxycurcumin (CAS number 33171-05-0). Curcumin (1,7-bis(4-hydroxy-3-methoxyphenyl)-1,6-heptadiene-3,5-dione), also known as diferuloylmethane (CAS number: 458-37-7), is the main curcuminoid of Asian curcuma.

The curcuma extract present in the combination is typically an extract of fresh or dry *Curcuma longa* L rhizome. It may be a standardized curcuminoid extract. The composition according to the present invention may contain a curcuminoid-standardized curcuma extract. For the purposes of the invention, the term "standardized" or "standardize" refers to the notion of controlling an extract, an oil or any other ingredient for the purpose of making it comply with a standard or with a given minimum content of certain molecules, for instance curcuminoids in the case of a curcuma extract. A curcuminoid-standardized curcuma extract is thus a curcuma extract having a defined minimum content of curcuminoids, preferably a minimum content of 15% of curcuminoids.

The curcuma extract present in the combination according to the invention may be obtained via any known extraction method, for example by extraction using an organic solvent, by maceration or decoction or alternatively by extraction with supercritical fluid. Preferably, it is a curcuma rhizome extract obtained via a process comprising a step of extraction with a solvent which may be used in the preparation of food supplements, for example an alcohol or an ester such as ethyl acetate.

Advantageously, the curcuminoid-standardized curcuma extract is used in powder form. Its water content is preferably less than 15% relative to the total weight of the extract. According to a preferred embodiment of the invention, the curcuma extract contains at least 10%, 15% or 20% of curcuminoids. More preferably, the curcuminoids of the extract are distributed as follows: between 65% and 82% of curcumin and, 15% to 25% of demethoxycurcumin and/or 2% to 7% of bisdemethoxycurcumin.

According to one embodiment, the curcuma extract comprises curcumin: CAS number 458-37-7, demethoxycurcumin: CAS number 22608-11-3, and bisdemethoxycurcumin: CAS number 33171-05-0.

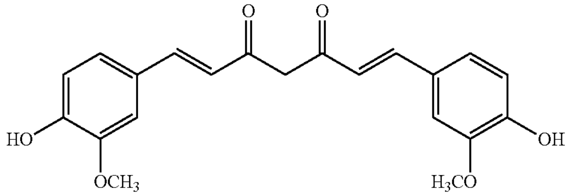

Curcumin

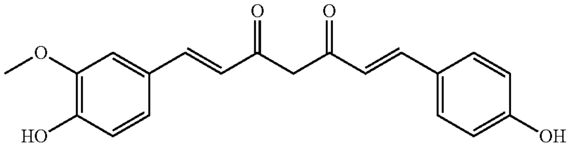

Demethoxycurcumin

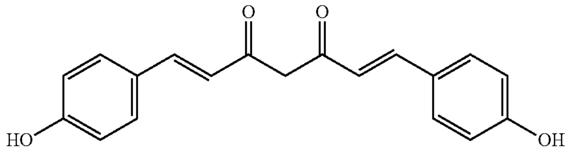

Bisdemethoxycurcumin

In order to improve the bioavailability of the curcuminoids, the curcuma extract may be formulated using a vector or an encapsulation system such as liposomes or cage molecules. In a particular embodiment, the curcuma extract is combined with a cyclodextrin, preferably a γ-cyclodextrin. It may notably be the product Cavacurmin® sold by Wacker.

In a particular embodiment, the curcuma extract is encapsulated with γ-cyclodextrin, in particular as defined under the CAS number 17465-86-0. According to a particular aspect, the curcuma extract is encapsulated in a cyclodextrin, preferably a γ-cyclodextrin, and/or the curcuma extract is combined with an encapsulation or vectorization system, preferably a cyclodextrin.

In a very particular embodiment:

the curcuma extract comprises at least 10% or 15% by weight of curcuminoids, and/or the curcuma extract comprises curcumin, demethoxycurcumin and bisdemethoxycurcumin, and/or the curcuma extract comprises at least 55% and preferably at least 60% by weight of curcumin relative to the total weight of the curcuminoids present in the extract, and/or the curcuma extract is encapsulated in a cyclodextrin, preferably a γ-cyclodextrin, and/or the curcuma extract is combined with an encapsulation or vectorization system, preferably a cyclodextrin.

According to one aspect, the composition thus comprises curcumin, which is introduced into the composition by adding a curcuma extract, or which is in a purified form.

The curcuma extract content of the composition according to the invention is advantageously less than 15% per 100% by weight of the three ingredients (glutamine, curcuma extract and *Lactobacillus rhamnosus*) or per 100% by weight of the composition. The curcuma extract content of the composition according to the invention is preferably from 1% to 15%, from 2% to 15%, from 3% to 15%, from 4% to 15%, from 5% to 15%, from 6% to 15%, from 7% to 15%, from 8% to 15%, from 9% to 15% or from 10% to 15%, preferentially 1% to 10%, from 2% to 10%, from 3% to 10%, from 4% to 10% or from 5% to 10%, and even more preferentially from 1% to 5%, from 2% to 5%, from 3% to 5% or from 4% to 5%, most preferably 4%, 4.1%, 4.3%, 4.4%, 4.5%, 4.6%, 4.7%, 4.8% or 4.9% per 100% by weight of the three ingredients (glutamine, curcuma extract and *Lactobacillus rhamnosus*) or per 100% by weight of the composition.

Preferentially, the composition according to the present invention contains from 3% to 10%, preferably from 4% to 9%, of curcuma per 100% by weight of the three ingredients: glutamine, curcuma extract and *Lactobacillus rhamnosus* or per 100% by weight of the composition.

According to a very particular embodiment, the composition according to the present invention contains from 4% to 8% of curcuma per 100% of the total weight of the composition.

According to another very particular embodiment, the composition according to the present invention contains from 4% to 5% of curcuma per 100% by weight of the three ingredients (glutamine, curcuma extract and *Lactobacillus rhamnosus*) or per 100% by weight of the composition.

The daily dose of curcuma extract may be between 25 mg and 500 mg.

*Lactobacillus rhamnosus* Bacterium

Some of the probiotic strains that have been the most extensively studied belong to the group of lactic acid bacteria (LAB). These bacteria are anaerobic or air-tolerant, generally non-sporulating Gram-positive microorganisms with a low genomic GC content, which produce lactic acid as the main final product of carbohydrate fermentation. LABs are generally acknowledged as being safe and some species have obtained the qualified presumption of safety (QPS) status of the European Food Safety Authority (EFSA).

The bacterial strain used in the composition according to the invention is a bacterial strain of the species *Lactobacillus rhamnosus*, in particular selected from the group consisting of *L. rhamnosus* GG (ATCC 53103), *L. rhamnosus* Lc705 (DSM 7061), *L. rhamnosus* CNCM 1-3690, *L. rhamnosus* CNCM 1-1720, *L. rhamnosus* la801, *L. rhamnosus* sp1, *L. rhamnosus* HN001 (NM97/09514), *L. rhamnosus* r0011, *L. rhamnosus* r0052, *L. rhamnosus* ha-111, *L. rhamnosus* jb-1, *L. rhamnosus* la801, *L. rhamnosus* 1r06, *L. rhamnosus* lr-32, *L. rhamnosus* Ibv96 and *L. rhamnosus* Icr35.

Preferably, the bacterial strain is *Lactobacillus rhamnosus* GG. This strain was deposited under the Treaty of Budapest at the American Type Culture Collection (ATCC) under the accession number ATCC 53103. It is understood that the present invention also relates to the use of any bacterium derived from the species *Lactobacillus rhamnosus*, and also to the use of any strain or homolog derived from this bacterial species. The terms "homolog", "variant" or "mutant" are interchangeable and refer to a bacterial strain having homology or sequence identity with the nucleotide sequence of the parent bacterial strain (the reference sequence). This includes bacterial strains having at least 95%, 96%, 97%, 98% or 99% identity with the nucleotide sequence of the genome of the species *Lactobacillus rhamnosus*, preferably with the nucleotide sequence of the genome of the strain *Lactobacillus rhamnosus* GG. The mutants may be obtained by genetic engineering techniques which make it possible to infer the alteration of the genetic material of the strains of the invention or to infer a recombination of the genetic material of the strains of the invention with other molecules. Typically, in order to obtain such mutant strains, a person skilled in the art can use standard mutagenesis techniques such as UV radiation or exposure to mutagenic chemical products.

The *Lactobacillus rhamnosus* content of the composition according to the invention is advantageously from 0.02% to 5%, from 0.05% to 5%, from 0.1% to 5%, from 0.25% to 5%, from 0.5% to 5%, from 0.5% to 4%, from 0.5% to 3%, from 0.5% to 2.5%, from 0.5% to 2%, from 0.5% to 1.5% or from 0.5% to 1%, preferentially from 0.5% to 1.5%, from 0.5% to 1.25% or from 0.5% to 0.75%, even more preferentially less than 1%, and most preferably 0.5%, 0.6%, 0.7% or 0.8%, per 100% by weight of the three ingredients (glutamine, curcuma extract and *Lactobacillus rhamnosus*) or per 100% by weight of the composition.

Preferentially, the composition according to the present invention contains from 0.25% to 5%, preferably from 0.3% to 4%, of *Lactobacillus rhamnosus* per 100% by weight of the three ingredients: glutamine, curcuma extract and *Lactobacillus rhamnosus* or per 100% by weight of the composition.

According to a very particular embodiment, the composition according to the present invention contains 0.3% to 0.6%, preferably from 0.4% to 0.5%, of *Lactobacillus rhamnosus* per 100% by weight of the three ingredients (glutamine, curcuma extract and *Lactobacillus rhamnosus*) or per 100% by weight of the composition.

The bacteria contained in the composition according to the invention may be live or inactivated. Preferably, the bacteria contained in the composition are in live form. They may notably be in a hydrated, lyophilized, frozen or atomized form or in any other form which enables them to be administered live to the individual. Said bacteria may be administered in unmodified form or after having been taken up in a suitable physiologically acceptable vehicle.

The bacteria are administered, for example, in the form of cultivated live bacteria, in vegetative form. Alternatively, the bacteria are supplied in the form of purified populations obtained from microbiotic material such as fecal material. The term "live" should be understood as meaning that the integrity of the cell is conserved and that the cell processes take place or are able to take place if the bacterium is cultivated in an adequate medium and under adequate conditions. Any live bacterium can be once again seeded onto an adequate culture medium and multiply, under adequate conditions.

The composition according to the invention preferably contains between $10^7$ to $10^{11}$, notably from $10^8$ to $10^{11}$, preferably from $10^9$ to $10^{11}$ colony-forming cells (CFU), preferably *Lactobacillus rhamnosus* cells per gram of composition. The term "CFU" means "colony-forming units". The term "gram of composition" preferably means the composition according to the invention comprising the bacteria according to the invention and the suitable co-ingredients, excipients or vehicles.

The daily dose of *Lactobacillus rhamnosus* may be between 0.05 mg and 500 mg or between $1\times10^7$ CFU and $1\times10^{11}$ CFU.

Additional Ingredients

The composition may also comprise:

- one or more prebiotics; and/or
- vitamins, minerals and/or trace elements; and/or
- powders or extracts of plants, fruit, vegetables, algae or fungi; and/or
- one or more probiotics.

The pharmaceutical, nutraceutical or food composition may also comprise one or more additional strains of microorganisms, notably microorganisms also used as probiotics. By way of example, the composition may comprise one or more additional strains of microorganisms chosen from the group consisting of *Bacillus, Bacteroides, Bifidobacterium, Enterobacteriaceae, Enterococcus, Faecalibacterium, Fusobacterium, Kluyveromyces, Lactobacillus, Odoribacter, Parabacteroides, Pediococcus, Ruminococcus, Streptococcus* and/or *Saccharomyces*.

In another embodiment, the composition exclusively comprises bacteria of the genus *Lactobacillus*. Preferably, the composition does not comprise any bacteria of the genus *Bifidobacterium* and/or a *Lactobacillus* species other than *rhamnosus*. In particular, the composition comprises, as probiotic, bacteria of the species *Lactobacillus rhamnosus* to the exclusion of any other microorganism, in particular any other probiotic bacterium and/or yeast.

In a particular embodiment, the pharmaceutical, nutraceutical or food composition comprises less than 20 different strains of microorganisms, preferably less than 10, 9, 8, 7, 6, 5, 4 or 3 different strains of microorganisms.

Moreover or in addition, the pharmaceutical, nutraceutical or food composition may also comprise one or more prebiotics.

According to one embodiment, the pharmaceutical, nutraceutical or food composition according to the invention comprises a probiotic in live form and also one or more prebiotics which can be degraded by the probiotic or the gut microbiota. This combination of prebiotic(s) and probiotic constitutes a symbiotic.

According to a particular aspect, the composition according to the invention may also comprise:

- vitamins, minerals or trace elements;
- powders or extracts (dry or liquid) of plants, fruit, vegetables, algae or fungi; and/or
- physiological substances for nutritional or health purposes, notably prebiotics, preferably as defined in the Order of Sep. 26, 2016 establishing the list of substances for nutritional or physiological purposes permitted in food supplements and the conditions for using same.

The vitamins, minerals and/or trace elements may be chosen, for example, from: a vitamin (thiamine (B1), riboflavin (B2), niacin (B3), pantothenic acid (B5), pyridoxin (B6), folic acid (B9) and cyanocobalamin (B12), and also vitamins C, A, D, E, K1 and K2, a mineral such as magnesium, calcium or iron, trace elements such as iodine, iron, copper, zinc, selenium, chromium, molybdenum, boron or manganese, or a mixture thereof.

The powders or extracts (dry or liquid) of plants, fruit, vegetables, algae or fungi may notably be chosen from the various European regulatory lists known to those skilled in the art, comprising, for example: konjac powder/extract, yam powder/extract, bean powder/extract, coffee powder/extract, tea powder/extract, pine bark powder/extract, grape powder/extract, garlic powder/extract, saffron powder/extract, apple powder/extract, reishi mushroom powder/extract, *spirulina* powder/extract, *chlorella* powder/extract, brown algae powder/extract and any mixture thereof.

In certain embodiments, the physiological substance for nutritional or health purposes is a prebiotic. The prebiotic may particularly be a carbohydrate polymer which is more or less branched and with a variable degree of polymerization. The prebiotic may be chosen, for example, from inulin, inositol, tagatose, lactulose, α-glucan oligosaccharide, transgalacto-oligosaccharides (TOS), fructo-oligosaccharides (FOS), galacto-oligosaccharides (GOS), xylo-oligosaccharides (XOS) and a mixture thereof.

In certain embodiments, the physiological substance for nutritional or health purposes is an amino acid such as, without being limited thereto, leucine, citrulline, glutamine, glutamate, cysteine and derivatives thereof, methionine and derivatives thereof, tryptophan and derivatives thereof.

In certain embodiments, the physiological substance for nutritional or health purposes is an antioxidant, for instance, without being limited thereto: superoxide dismutase (SOD), ubiquinol/ubiquinone (coenzyme Q10), resveratrol, catechins (catechin, epicatechin and gallate derivatives), flavanols, flavanones or anthocyans.

Nutraceutical Composition

According to a particular aspect, the composition is a nutraceutical composition. The term "nutraceutical composition" means any composition comprising food ingredients such as macronutrients, micronutrients, plants or plant extracts, or substances with a nutritional or physiological effect, directed toward supplementing the diet of a human being in order to improve his or her nutritional status and thus to promote a good state of health. As envisaged herein, nutraceutical products are isolated nutrients, food supplements or are included in certain foods intended for specific groups. Nutraceutical compositions thus cover compositions comprising glutamine, curcuma extract and *Lactobacillus rhamnosus* probiotic bacteria and a food-grade component, in particular a technological additive or auxiliary.

Food Composition

According to a particular aspect, the composition is a food composition. The term "food composition" means any composition comprising food ingredients such as macronutrients, micronutrients, vitamins, minerals, trace elements or substances with a nutritional or physiological effect. As envisaged herein, the food products are conventional foods, functional foods or processed foods. Thus, by definition, the food compositions may be diverse and varied foods, known to those skilled in the art.

The food composition may notably be a food intended for human food or animal feed, which may be a liquid, a paste or a solid. As examples, without being limited thereto, the food may be a dairy product such as cheese, butter, cream, yoghurt, ice cream or cheese, cooked products such as bread, biscuits and cakes, a fruit-based product such as a fruit juice, a compote or a fruit jelly, soya-based food products, starch-based food products, confectionery products, compositions for edible oils, spreads, breakfast cereals, infant preparations, juices, food bars (for example cereal bars, breakfast bars, energy bars or nutritional bars); biscuits, snacks, chewing gums, drinks; energy drinks, enriched drinks; drinkable supplements (powders to be added to a drink); etc.

According to a particular aspect, the food composition is not milk-based. Preferably, the food composition does not comprise any human or animal milk protein(s) or oligosaccharide(s).

Thus, the food composition according to the invention comprises glutamine, a curcuma extract and the bacterium *Lactobacillus rhamnosus* and the components of at least one of the foods or drinks mentioned previously.

The invention also relates to a method for preparing a nutraceutical composition, comprising the addition of glutamine, of curcuma extract and of a strain of *Lactobacillus rhamnosus*, in particular as active principle, to the components of the nutraceutical composition. The invention also relates to a method for preparing a food composition, comprising the addition of glutamine, of curcuma extract and of a strain of *Lactobacillus rhamnosus*, in particular as active principle, to the components of the food composition.

The invention also relates to a method for improving the mental well-being or reducing the mood disorders of an individual, comprising the administration of a nutraceutical or food composition comprising an effective amount of glutamine, of curcuma extract and of a strain of *Lactobacillus rhamnosus*.

The invention relates, moreover, to a nontherapeutic use of the nutraceutical or food composition according to the invention as defined previously, for the preparation of compositions intended for improving the mental well-being of an individual.

Pharmaceutical Composition and Drug

The composition according to the invention may in particular be a pharmaceutical composition intended for use in human medicine or for veterinary use.

The pharmaceutical composition according to the invention comprises a combination of glutamine, of curcuma extract and of a strain of *Lactobacillus rhamnosus* as active principle. In one embodiment, the pharmaceutical composition may also contain at least one additional pharmaceutical active principle. The term "pharmaceutical active principle" means any compound or substance whose administration has a therapeutic effect or a beneficial effect on the health or general condition of a patient or of an individual to whom it is administered. In one embodiment, the other pharmaceutical active principle is not a probiotic bacterium, in particular a strain of Bifidobacteria and/or a *Lactobacillus* species other than *rhamnosus*. For example, the additional active principle(s) might be an antidepressant drug or an anxiolytic drug. Alternatively, the other pharmaceutical active principle contained in the pharmaceutical composition is a probiotic strain or a combination of probiotic strains. By way of example, the composition may comprise one or more additional strains of microorganisms chosen from the group consisting of bacteria of the genera *Bacillus, Bacteroides, Bifidobacterium, Enterobacteriaceae, Enterococcus, Faecalibacterium, Fusobacterium, Kluyveromyces, Lactobacillus*, Odoribacter, Parabacteroides, *Pediococcus, Roseburia, Ruminococcus, Saccharomyces* and *Streptococcus.*

The present invention also relates to a combination of glutamine, of curcuma extract and of a strain of *Lactobacillus rhamnosus* for use as a drug, preferentially for use as a drug in the field of psychiatry, in particular for regulating anxiety disorders and/or mood disorders such as depression, preferably for reducing anxiety and/or depression and/or the mixed anxiety and depressive symptoms associated therewith.

In particular, the present invention relates to a composition according to the invention, preferably a pharmaceutical composition, for use in the treatment of an anxiety disorder and/or a mood disorder such as depression, and the mental and/or behavioral symptoms associated therewith; the use of a composition according to the invention for the preparation of a drug intended for treating an anxiety disorder and/or a mood disorder, particularly depression, and/or the mental and/or behavioral symptoms associated therewith; and a method for treating an anxiety disorder and/or a mood disorder, particularly depression, and/or the mental and/or behavioral symptoms associated therewith, in an individual, comprising the administration of a therapeutically effective amount of a composition according to the invention, preferably a pharmaceutical or nutraceutical or food composition, to said individual. Preferably, said individual has been diagnosed beforehand as having anxiety disorders and/or mood disorders, in particular depression, or is at risk of developing one of these disorders.

The composition according to the invention may be used in combination with another active principle, for example an antidepressant drug or an anxiolytic drug. Thus, the present invention also relates to a composition for its use in treating an anxiety disorder and/or a mood disorder, particularly depression, and/or the mental and/or behavioral symptoms associated therewith, in combination with an antidepressant drug or an anxiolytic drug. The invention also relates to a method for treating an anxiety disorder and/or a mood disorder, particularly depression, and/or the mental and/or behavioral symptoms associated therewith, in an individual, comprising the administration of a therapeutically effective amount of a composition according to the invention to said individual and the administration of a therapeutically effective amount of an antidepressant drug or an anxiolytic drug.

Formulation of the Composition

The formulation of a pharmaceutical, nutraceutical or food composition according to the present invention may vary as a function of the administration route and of the dosage for which the composition is intended to be used. The pharmaceutical, nutraceutical or food composition according to the invention may notably be in solid, semisolid or liquid form. After formulation with at least one physiologically acceptable vehicle or excipient, a composition according to the invention may be in any form that is suitable for administration to a mammal, in particular man, for example in the form of lozenges, tablets, pastilles, sugar-coated tablets, hard capsules, soft gel capsules, pills, granules, powder, suspensions, emulsions, syrups, ointments, a vial of liquid, a bottle equipped with a dropper and other similar forms of liquid or powder preparations, or suppositories.

A person skilled in the art knows how to select the vehicles and excipients that are the most suitable for the preparation of a given type of formulation.

In a particular embodiment, the physiologically acceptable vehicle may be a solid and the composition according to the invention may be in the form of a powder or a tablet. The physiologically acceptable vehicle may alternatively be a liquid, and the composition according to the invention is in the form of a solution. The liquid vehicles are used in the preparation of solutions, solvents, dispersion media, suspensions, emulsions, syrups, elixirs and compositions under pressure. The appropriate liquid supports or gel-based supports comprise, without being limited thereto: water and physiological saline solutions; emulsions or suspensions, including saline solutions and buffered media, urea; alcohols (for example ethanol), and nonaqueous solvents such as vegetable oils or seed oils such as olive oil. The liquid compositions, for example including emulsions, microemulsions, solutions, suspensions, syrups or elixirs, may notably be formulated in the presence of solvents, solubilizers, emulsifiers, oils, fatty acids, and/or other additives, for instance suspension agents, preserving agents, sweeteners, natural or synthetic flavorings, viscosity enhancers, stabilizers and/or thickeners and/or coloring agents of food grade, which must all be compatible with maintaining the viability of the *Lactobacillus rhamnosus* strain. The emulsions may contain emulsifiers such as lecithin, sorbitan monooleate or acacia. Well-known thickeners may also be added to the compositions, such as maize starch, natural or synthetic gums, resins, methylcellulose, sodium carboxymethylcellulose, guar gum, xanthan gum and the like. The composition of the excipient may be modified as long as it does not interfere significantly with the pharmacological activity of the *Lactobacillus rhamnosus* probiotic bacteria according to the invention.

In particular, the composition according to the invention may also comprise:

- anticaking agents such as magnesium carbonate, silicon dioxide or stearic acid;
- one or more viscosity agents or surfactants, notably starch, cellulose ethers such as hydroxypropylmethylcellulose or acacia gum;
- one or more binders, notably fish oil or any plant oil, for instance sunflower oil, soybean oil, olive oil or chia oil;
- coating agents such as beeswax, carnauba wax or dietary fatty acid monoglycerides;
- emulsifiers such as lecithin, cyclodextrins or ester gum;
- one or more non-nutritive sweeteners, notably sorbitol, sucralose, aspartame, neotame, maltitol, xylitol, acesulfame-K, aspartame, saccharine, glycyrrhizic acid or a *Stevia* extract;
- one or more natural or artificial flavouring agents, in pulverulent or liquid form;
- one or more acidity correctors, notably salt, citric acid, malic acid or tartaric acid; and/or
- one or more colorants, notably anthocyans, β-carotene, beetroot extract, lycopene or caramel extract.

In certain embodiments, a pharmaceutical, nutraceutical or food composition according to the present invention is formulated for immediate release of the active principle(s). Alternatively, a pharmaceutical composition may be formulated for sustained or targeted release of the active principle (s) or for protection of the active principle(s), for example with respect to gastric acidity and gastric enzymes. It is thus possible to use pH-resistant coatings and/or coatings that are resistant to the action of gastric enzymes, pH-sensitive coatings and/or coatings that are sensitive to enzymatic actions, or bioadhesive coatings which attach to the walls of the stomach or of the intestine, or encapsulation systems.

Preferably, the composition according to the invention is a composition in a form that is suitable for oral administration. It may notably be in the form of pills, tablets, gel capsules or powders optionally to be dissolved or resuspended in a suitable vehicle, pastes or gums for chewing, sweets for sucking or chewing, solutions, for example drinkable solutions packaged in vials, gels, etc.

Preferably, the composition is in a gastro-resistant oral form enabling the bacteria contained in the composition according to the invention to pass through the stomach and to be released in the intestine. An enteric coating may be stable at acidic pH (such as in the stomach) and can dissolve at a basic pH (for example in the intestine). The material that may be used in enteric coatings comprises, for example, alginic acid, cellulose acetate phthalate, waxes, shellac, fatty acids (for example stearic acid or palmitic acid) or chitosan, in a nonexhaustive manner.

In one embodiment, the gastro-resistant and entero-soluble coating is designed to maintain the stability of the active ingredients in the stomach. The enteric coating is designed to be maintained under the acidic conditions of the stomach and to degrade under nonacidic conditions, thus releasing the pharmaceutical, nutraceutical or food composition into the intestines.

The enteric coatings may be used for i) preventing the gastric juices from reacting with or destroying the active substance, ii) preventing the dilution of the active substance before it reaches the intestines, iii) ensuring that the active substance is not released until after passing the preparation through the stomach, and iv) preventing the live *Lactobacillus rhamnosus* bacteria contained in the composition according to the invention from being altered or killed by the acidic pH of the stomach.

According to one embodiment, the composition may also comprise maltodextrin and/or magnesium stearate. In particular, the composition may be formulated according to one of the examples described below.

In a particular embodiment, the composition according to the invention is in the form of dose units comprising:

between 0.5 g and 10 g and preferably between 0.5 g and 2 g of glutamine, between 25 mg and 500 mg and preferably between 50 mg and 100 mg of curcuma extract, and between 0.05 mg and 500 mg, preferably between 10 mg and 20 mg, or between $1\times10^{7}$ CFU and $1\times10^{11}$ CFU of *Lactobacillus rhamnosus*, preferably *Lactobacillus rhamnosus* GG.

The dose units may be, for example, tablets and gel capsules.

In a particular embodiment, the dose units are included in a single sachet containing two compartments. The first compartment comprises the *Lactobacillus rhamnosus* bacteria and the other compartment comprises the glutamine and the curcuma extract, for example in the form of powders.

An additional subject according to the invention is an administration kit, a nutraceutical or pharmaceutical kit, for example a food supplement kit comprising several compositions, which are preferably intended for oral administration, incorporating the combination according to the invention.

A subject of the invention is thus also a kit, preferably a pharmaceutical, nutraceutical or food kit, comprising the combination of glutamine, a curcuma extract and *Lactobacillus rhamnosus*, said kit being suitable for individuals who are suffering from or who are liable to suffer from emotional disorders.

In a particular embodiment, said kit comprises:

a composition comprising the *Lactobacillus rhamnosus* bacterium, a composition comprising glutamine, and a composition comprising curcuma extract.

For example, the glutamine, the curcuma extract and the *Lactobacillus rhamnosus* bacterium may be administered in the form of a kit, i.e. in the form of several separate pharmaceutical, nutraceutical or food compositions, for example in the form of at least two dose units for oral administration, for example a first gel capsule containing *Lactobacillus rhamnosus* and a tablet or a second gel capsule containing the glutamine and the curcuma extract.

In a particular embodiment, the administration kit may take the form of a single sachet containing two compartments which are intended to receive the different ingredients of the composition according to the invention. Preferably, the first compartment comprises the *Lactobacillus rhamnosus* bacteria and the other compartment comprises the glutamine and the curcuma extract.

The kit for administering the combination may alternatively comprise three separate gel capsules, one gel capsule containing the bacteria, one tablet or gel capsule containing the glutamine and one tablet or gel capsule containing the curcuma extract.

In a particular embodiment, the administration kit may take the form of a single sachet containing three compartments which are intended to separately receive each of the three different ingredients of the composition according to the invention.

In a particular embodiment, the kit comprises:

a first composition comprising the bacterium *Lactobacillus rhamnosus*, for example combined with one or more excipients, a second composition comprising glutamine and the curcuma extract, for example combined with one or more excipients.

Each of these two compositions may be in the form of a gel capsule, a tablet or a powder.

The kit typically comprises several dose units of each composition. It may also comprise instructions for administering the kit.

In a particular embodiment, the first composition may be in the form of dose units comprising between 0.5 and 10 g of glutamine, between 25 mg and 500 mg of curcuma extract and between 0.05 mg and 500 mg or between $1\times10^{7}$ CFU and $1\times10^{11}$ CFU of *Lactobacillus rhamnosus*. The dose units may be, for example, tablets and gel capsules.

The features of the compositions present in this kit are similar to those of the composition according to the invention, notably in terms of relative mass ratio of *Lactobacillus rhamnosus*, glutamine and curcuma extract.

Each composition present in the kit may comprise one or more additional ingredients chosen from additional additives, excipients and active agents which are pharmaceutically, nutraceutically and/or nutritionally acceptable as described above.

Individual and Administration Regimen

The pharmaceutical, nutraceutical or food composition according to the invention may be employed for human or animal medical or nutritional purposes, the individual under consideration notably possibly being a mammal, more particularly any animal subject such as a laboratory animal (for example a non-human primate, rat, mouse, hamster or guinea pig), a livestock animal (for example a cow, sheep, goat, pig, turkey or hen) or a domestic species (for example a dog, cat or rodent), and even more particularly a human, for example a child or an adult.

According to the invention, the term "child" means an individual less than 18 years old. Thus, the category of children according to the invention includes newborn, which are between 0 and 1 month old, infants, which are between 1 month and 2 years old, and children per se, which are at least 2 years old. The term "adult" means any person of at least 18 years old.

The pharmaceutical, nutraceutical or food compositions according to the present invention may be administered using any combination of dosage and of administration route that is effective for obtaining the desired therapeutic effect. The exact amount to be administered and the frequency of administration will notably depend on the type of human or animal individual, as a function of the age, weight and general condition of the patient or of the animal, and on the nature and seriousness of the disorder. The administration route may be chosen as a function of the intensity of the disorder and/or as a function of the age and/or health of the patient.

In a particular aspect, for an adult, the composition is intended to be administered such that the daily dose of the composition is between 0.5 and 10 g, preferably between 1 and 5 g. Notably, the daily dose of glutamine may be between 0.5 and 10 g, and/or the daily dose of curcuma extract may be between 25 mg and 500 mg, and/or the daily dose of *Lactobacillus rhamnosus* may be between 0.05 mg and 50 mg or between $1\times10^7$ CFU et $1\times10^{11}$ CFU.

The composition according to the invention may be administered in one or more goes, i.e. in the form of a single dose or of multiple doses.

A dose may represent several milligrams to several tens of grams of composition according to the invention. Typically, a dose represents between 1 mg and 100 mg, between 1 mg and 1 g, between 1 mg and 10 g, between 10 mg and 100 mg, between 10 mg and 1 g, between 10 mg and 10 g, between 100 mg and 1 g, between 100 mg and 10 g or between 1 g and 10 g of composition according to the invention, preferably between 100 mg and 10 g of composition according to the invention, and more particularly preferably between 500 mg and 5 g of composition according to the invention.

The composition according to the invention may be administered to an individual before the onset of the symptoms (i.e. prophylactically, for example before the occurrence of an anxiety-generating situation) or after the onset of acute or chronic symptoms (i.e. for therapeutic purposes, for example after the onset of mixed anxiety and depressive symptoms). The composition according to the invention may thus be administered at any moment and at any interval. Thus, in certain embodiments, the administration of the pharmaceutical, nutraceutical or food composition, of the drug, of the food supplement or of the food according to the invention is episodic.

In another embodiment, the administration of the composition, of the drug, of the food supplement or of the food according to the invention is at regular intervals. Preferably, the composition is administered to an individual at a frequency of between one dose per day and one dose per month. Typically, the frequency of administration is between one or several doses per day and one dose per week, for example one dose every 2, 3, 4, 5, 6 or 7 days. Alternatively, the frequency of administration may be several doses per day, for example 2, 3, 4 or 5 doses per day, or else only one dose (monodose). Depending on the age and physiological state of the individual, the daily doses may be fractionated to facilitate the administration, for example with one administration in the morning and another in the evening.

In one embodiment, the composition is administered for about 24 hours, about 2 days, about 5 days, about 10 days, about 15 days, about 30 days or 1 month, about 2 months, about 4 months, about 6 months, or about 1 year after the initial onset of the symptoms (for example symptoms associated with the depressive state) and/or after the diagnosis of a disorder (for example depression) in the individual.

The composition according to the invention, the drug, the food supplement or the food may be administered via various routes, preferably the enteral route comprising, but not necessarily limited to, oral or intranasal administration. According to a particular embodiment of the invention, the composition, the drug, the food supplement or the food is administered orally. In a particular embodiment, the drug or the nutraceutical or food composition is administered via a stomach tube.

The Psychiatric Disorders Targeted by the Invention

The invention relates to the regulation of the emotional state of an individual, the prevention and/or treatment of anxiety disorders and/or a mood disorder such as depression, and/or mixed anxiety-depressive disorders, and/or the mental and/or behavioral symptoms associated therewith. The individual may notably be predisposed to such a state or may show one or more symptoms of such a state. The invention also relates to prevention of the onset of a depressive or anxiety episode in an individual.

Mood disorders, often associated with anxiety, may be any psychological state associated with one or more somatic or psychosomatic symptoms. In certain cases, the development of a mood disorder, in particular depression, is associated with or characterized by a symptom such as sadness, irritability, restlessness, fatigue, weight loss, problems with concentrating, memorizing and/or taking decisions, self-pity, changes in appetite or weight, sleep disturbance, feelings of guilt and/or hopelessness, addiction, lack of energy, lack of interest or pleasure, indecision, brooding, introversion, lack of self-esteem, suicidal thoughts or tendencies, tension, mood swings, slowed thinking and/or speech, feelings of uselessness, helplessness, anger, hostility, difficulty in thinking, concentrating or taking decisions, and/or tearfulness. These symptoms may also result in a somatic manifestation, comprising weepiness, shortness of breath, perspiration, nausea, rapid heartbeat, gastrointestinal function disorders and raised blood pressure.

The level of anxiety or depression in an individual can be established by means of a "symptom assessment scale". This term refers to one of the many standardized questionnaires, clinical instruments or symptom inventories used for measuring symptoms and symptom severity in an individual's emotional state disorders.

The depression assessment scales include, without, however, being limited thereto, those defined in the Diagnostic and Statistical Manual of Mental Disorders IV-text revision (DSM-IV-TR), the Mini-Mental State Examination (MMSE), the Hamilton Depression Rating Scale (HAMD-28 or HAMD-7), the 17-item Hamilton Depression Rating Scale (HRS 17), the Clinical Global Impression (CGI) scale, the Self-Rated Quick Inventory of Depressive Symptomatology (QIDS-SR 16), the Montgomery-Asberg Depression Rating Scale (MADRS), the Beck Depression Inventory (BDI), the Zung Self-Rating Depression Scale, the Geriatric Depression Scale (GDS), the Wechsler Depression Rating Scale, the Raskin Depression Rating Scale, the Inventory of Depressive Symptomatology (IDS), and the Quick Inventory of Depressive Symptomatology (QIDS). For example, the DSM-IV-TR system for diagnosing major depressive disorder requires the presence of at least five of the nine depressive symptoms, notably a depressed mood, decreased interest or pleasure, significant weight loss or gain, sleep disturbance (for example insomnia or hypersomnia), psychomotor agitation or slowing, fatigue or loss of energy, a feeling of worthlessness or of excessive guilt, decreased concentration, and the development of suicidal thoughts. Preferably, the symptoms should be present for a given period of time and with significant severity.

The anxiety rating scales include, but are not limited to, the State-Trait Anxiety Inventory (STAI), the Hamilton Anxiety Rating Scale (HAM-A), the Beck Anxiety Inventory (BAI), and the Hospital Anxiety and Depression Scale (HADS-A).

These rating scales may involve patient self-assessment or may involve scoring by a clinician. A reduction of 50% or more in the depression or anxiety scale score in the course of a clinical test (starting point to end point) is generally considered as being a favorable response for the majority of the depression and anxiety symptom rating scales.

"Remission" in the clinical studies of depression or anxiety often consists in obtaining a particular numerical assessment score or less than said score on an anxiety symptom rating scale (for example less than or equal to 39 on the STAI; or less than or equal to 9 on the BAI; or less than or equal to 7 on the HADS-A) or depression (for example less than or equal to 7 on the SDRH 17; or less than or equal to 5 on the QIDS-SR 16 or less than or equal to 10 on the MADRS).

According to one aspect, administration of the composition according to the invention makes it possible to improve and/or reduce the scores for the anxiety or depressive state rating tests. For example, a score of 0 to 7 on the HAMD scale is generally considered as being normal. Scores of 20 or more indicate moderate, severe or very severe depressive symptoms. Thus, a reduction in symptoms may be considered as being clinically relevant if, for example, the HAMD score is reduced to less than 20.

The reference to the treatment and prevention of depression, anxiety, or a depressive or anxiety-related disorder, as used herein, includes, inter alia, the at least partial inhibition or alleviation of one or more symptoms of the anxiety disorder and/or of the mood disorder, in particular related to depression, notably as described above.

According to one embodiment, the invention thus relates to the use of a pharmaceutical, nutraceutical or food composition comprising a combination of three ingredients, namely glutamine, curcuma extract and *Lactobacillus rhamnosus* bacteria, intended for the treatment of the human or animal body. This composition is suitable for the prevention and/or treatment of anxiety disorders and/or mood disorders, whether they are chronic or acute. More particularly, this composition is suitable for the prevention and/or treatment of anxiety disorders and/or mood disorders, in particular depression and/or mixed anxiety-depressive disorders, and/or the mental and/or behavioral symptoms associated therewith.

The invention also relates to a method for preventing or treating anxiety disorders and/or mood disorders, in particular depression and/or mixed anxiety-depressive disorders, and/or the mental and/or behavioral symptoms associated therewith in an individual, the method comprising the administration of a therapeutically effective amount of the composition according to the invention.

The invention also relates to a method for preventing or treating anxiety disorders and/or stress.

The therapeutically effective or sufficient amount of a composition according to the invention, is an amount which makes it possible to obtain the desired effect, namely an effect promoting a regulation or a reduction of anxiety disorders and/or mood disorders, in particular, a reduction of the symptoms associated with depression and/or anxiety. Alternatively, the therapeutically effective or sufficient amount of a pharmaceutical composition according to the invention, is an amount which makes it possible to improve an individual's mental well-being or to improve an individual's mental rating scale scores as described above.

In a method for treating an anxiety disorder and/or a mood disorder, a "therapeutically effective amount" of a composition is an amount which reduces the severity of a symptom and/or reduces a measurable parameter associated with the disorder by at least about 10%, at least about 20%, at least about 30%, at least about 40%, at least about 50%, at least about 60%, at least about 70%, at least about 80%, or at least about 90% or more, in comparison with the symptom (for example the severity of the symptom), or in comparison with the measurable parameter, in the absence of treatment of the individual or in comparison with a prior emotional state of the individual.

The present invention particularly relates to a method for treating an anxiety disorder and/or a mood disorder, in particular anxiety and/or depression. The treatment methods according to the invention generally involve administering to an individual in need thereof an effective amount of a formulation comprising glutamine, curcuma extract and bacteria of the species *Lactobacillus rhamnosus*, as described above, for either curative or preventive purposes in order to decrease, limit or delay the onset and/or severity of emotional symptoms. The methods for treating an anxiety disorder and/or a mood disorder comprise methods for treating individuals who have been diagnosed with an emotional disorder, in particular anxiety and/or depression; methods for reducing the incidence of recurrence, or "flare-up" of the disorder; methods for reducing the risk of developing symptoms associated with emotional disorders in individuals who have been diagnosed with an emotional disorder and who have been treated with conventional treatments and are in remission; and processes for treating an anxiety disorder and/or a mood disorder in an individual who has not responded favorably to a conventional therapy for treating the diagnosed disorder. The methods for treating an anxiety disorder and/or a mood disorder also comprise methods for treating at-risk individuals. An individual who is "at risk" of a depressive and/or anxiety symptom includes individuals who are likely to develop mixed anxiety-depressive symptoms (for example individuals who are genetically predisposed or who are facing a tragic event that may give rise to such a state), an individual in remission from a depressive and/or anxiety symptom and who is now diagnosed with a relapse or predisposition to relapse.

Consequently, certain embodiments of the processes for treating or preventing a depressive or anxiety symptom described herein comprise the diagnosis of the individual as having a depressive or anxiety symptom, or who is at risk of developing the depressive or anxiety symptom, for example, prior to commencing the administration of the composition comprising according to the invention. In certain embodiments, the composition is administered to an individual who is being screened for a depressive or anxiety symptom, for example, in accordance with one of the tests described previously. The diagnosis may notably be made by means of scales for evaluating an individual's emotional state as described above.

The composition according to the invention may also have an influence on other conditions, disorders or symptoms for which emotional disorders are associated. For example, depression is associated, inter alio, with a state of fatigue and sadness. Thus, treatment of depression according to the treatment method of the invention also reduces the symptoms associated therewith, such as a reduction in feelings of sadness or fatigue. The methods of the invention may thus be applied as a prophylactic measure for preventing or reducing the risk of occurrence of symptoms caused by depression and/or anxiety.

The composition according to the invention may be combined with conventional agents used for treating depression and/or anxiety, where appropriate. These agents may alternatively be agents known as antidepressants or anti-anxiolytic agents, notably imipramine-based antidepressants, selective serotonin, norepinephrine or norepinephrine reuptake inhibitors or monoamine oxidase inhibitors. In one embodiment, these agents may optionally be administered in a subtherapeutic amount.

Such additional agents may be administered separately or included in the composition according to the invention.

In certain cases, the composition according to the invention is administered as an adjunct therapy, the individual being treated with psychotherapy. In certain embodiments, the method of treatment with the composition according to the invention also comprises treating the individual with psychotherapy.

As used herein, "psychotherapy" refers to non-pharmacological therapy in which the individual is psychologically engaged, directly or indirectly (for example through dialogue), for the purpose of restoring a normal psychological state; reducing the risk of developing a mood disorder and symptoms associated therewith; and/or for alleviating a mood disorder and symptoms associated therewith.

EXAMPLES

The solutions were administered orally by gastric intubation to mice (1 tube-feed per day).

The concentrations administered daily orally by gastric intubation are indicated in table 1.

TABLE 1

Table 1 Amount of starting materials administered by gastric intubation to the mice

| Starting materials | Daily amount Mouse (35 g) |
|---|---|
| Glutamine | 24 mg |
| Curcuma extract | 1.2 mg |
| *Lactobacillus rhamnosus* GG | 0.120 mg |

The preparation of the solutions is performed extemporaneously and the administration is performed in the morning. During the behavioral sessions, the solutions are administered one hour before the start of the session. The gastric incubation always takes place in a different room from the one in which the behavioral test is performed.

In order to evaluate the results obtained with the solutions, one group of mice received a parenteral administration of a tricyclic antidepressant (clomipramine). The mice were divided into independent groups according to the following treatments:

TABLE 2

Table 2 Division of the animals (n = 12 per group)

| Groups (n = 12 per group) | TREATMENTS |
|---|---|
| Control | / |
| Control | Placebo |
| Induced model | Placebo |
| Induced model | Glutamine |
| Induced model | *Lactobacillus rhamnosus* GG |
| Induced model | Curcuma extract |
| Induced model | Curcuma extract + Glutamine |
| Induced model | *Lactobacillus rhamnosus* GG + Glutamine |
| Induced model | Curcuma extract + *Lactobacillus rhamnosus* GG |
| Induced model | Curcuma extract + *Lactobacillus rhamnosus* GG + Glutamine |
| Induced model | Clomipramine (10 mg/kg) by intraperitoneal injection |

For each group, the administration of the various solutions lasts 21 consecutive days (3 weeks). The behavioral tests are performed 4 weeks after induction of the model ("elevated plus maze" and "tail suspension") and 3 weeks after the daily intubations ("open field" and "forced swim"). The way in which the study was conducted is presented in FIG. 1.

The Tests

The elevated plus maze (EPM) test is conventionally used for evaluating the reactivity of anxiety type in rodents (Can A., et al. J. Vis. Exp. 2012; 59:e3769). The elevated apparatus is 60 cm tall and is composed of two opposite open arms (30 cm long, 7 cm wide) and two opposite perpendicular closed arms (closed with a wall 17 cm high). The maze is placed in a room with a lighting of 70 lux. At the start of the session, mice were placed at the center of the plus-maze in a PVC cylinder for 20 seconds to allow random orientation at the start of the exploration. Next, after a waiting period of 10 seconds in the cylinder, the mice were permitted to explore the maze freely for 8 minutes. In the course of each session, the time spent in the open arms was measured and the percentage of the time spent in the open arms was calculated according to the following formula (time ratio:time in the open arms/time in all the arms)×100). All the parameters were automatically noted by videotracking (ViewPoint®, France).

The tail suspension test (TST) is a test commonly used for evaluating depressive behavior in mice (Steru L, et al. Psychopharmacology (Berl) 1985; 85(3):367-70). As in the forced swim test, this test is also based on behavioral despair. This test consists in attaching the animal by the tail with adhesive tape (head downward: 35 cm from the ground) for 5 minutes. In the course of this session, the immobility (seconds) and the percentage of the immobilization time, which is an indicator of depressive behavior in the rodent, were measured.

The open field test is a circular arena (ø 1 m) surrounded by an opaque wall 25 cm tall placed in a room with uniform lighting of 70 lux. The mice are placed facing the wall at the periphery of the arena and can explore freely for 5 minutes. The area of the open field is practically divided into a peripheral zone (12 cm wide) and a central zone (the remaining area of the arena). The time (in seconds) spent in the central zone is automatically noted by videotracking. The more time a mouse spends in the central zone, the less anxious it is.

The forced swim test (Porsolt) is a test commonly used for evaluating depressive behavior in mice. This test is based on behavioral despair. This test consists in placing the animal in a cylindrical glass basin (ø 15 cm) filled with water (30 cm high, 25±1° C.) for 6 minutes during which the animal can swim, climb or remain immobile. An animal displaying depressive behaviour will spend more time immobile than the non-depressive control mouse. After the session, the animal is dried and placed under warm light. Three parameters for evaluating the depressive behaviour are noted: the time spent swimming, the time spent climbing and the time spent immobile for each animal and also their respective percentage.

Results

Validation of the Model of Anxiety and Depression

After 4 weeks of induction of the anxiety by unpredictable stresses, the inventors evaluated the reactivity of the mice to these induced anxiety tests (UCMS) relative to two control groups paired according to age: unstressed mice which will not be treated, unstressed mice which will be subjected to a placebo gastric intubation.

Anxiety

The anxiety was measured by performing an "elevated plus maze" test as defined above.

Figure 2:
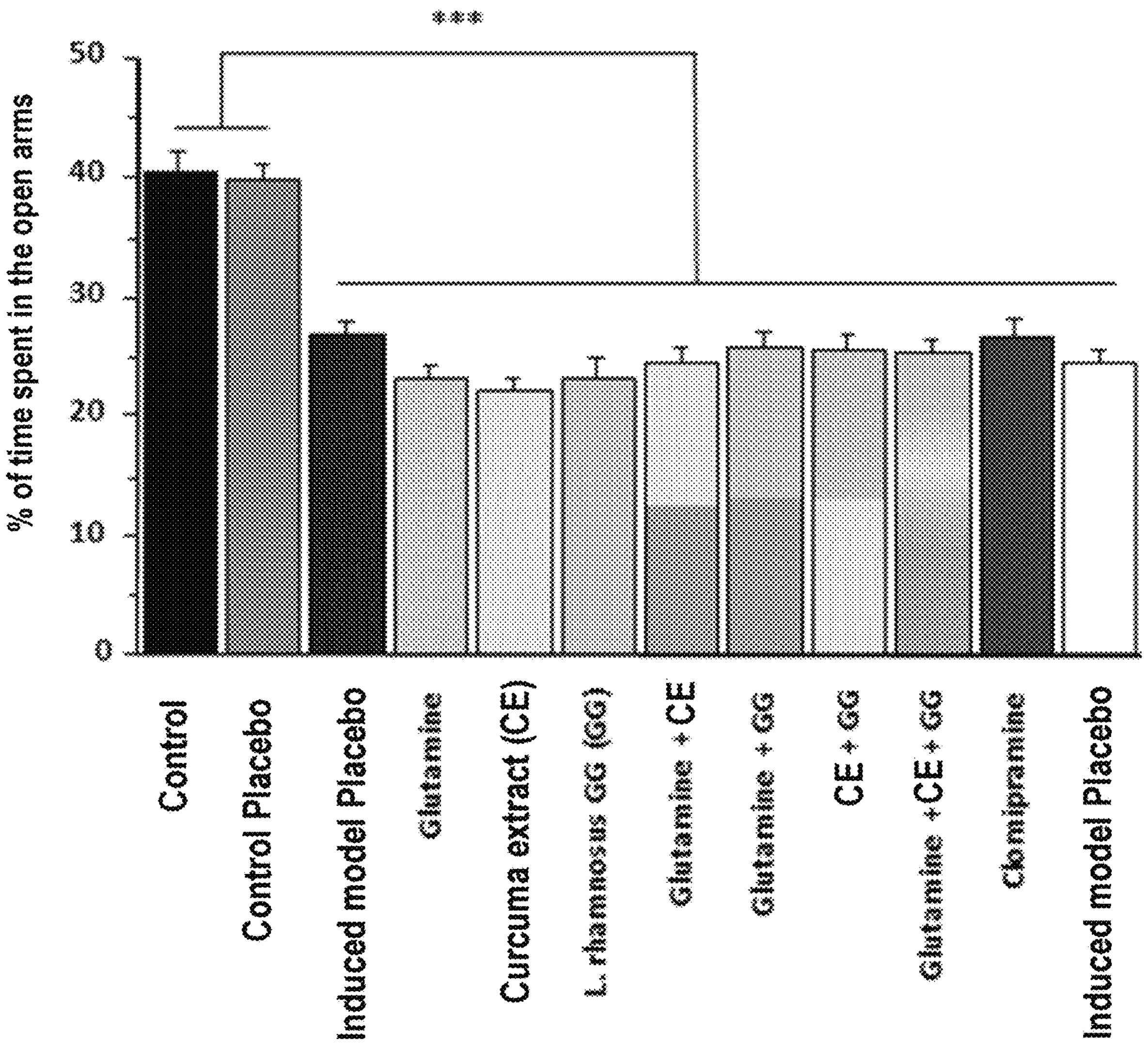
FIG. 2 represents the percentage of time in the open arms during the "elevated plus maze (EPM)" test. The results are the means±standard deviation. *** $p<0.001$ vs "control" and "control+placebo".

In FIG. 2, the data are presented as a function of the subsequent attribution of the various groups of phase 2, even if no treatment was administered during the current phase 1. It is demonstrated that the time spent in the open arms of the system is significantly reduced in the case of the stressed animals versus the unstressed animals ($p<0.001$).

TABLE 3

Table 3: Results of the "Elevated maze" test The results are the means ± standard deviation. SEM = Standard Error of Mean

| Elevated plus maze | | | | |
|---|---|---|---|---|
| Group (n = 12) | Time in open arm (seconds) | SEM | Time in closed arm (seconds) | SEM |
| Control | 194.2 | 8.4 | 285.8 | 8.4 |
| Control + Placebo | 191.6 | 6.0 | 288.4 | 6.0 |
| Model + Placebo | 128.5 | 4.9 | 351.5 | 4.9 |
| Model +*L. rhamnosus* GG | 111.3 | 8.8 | 368.8 | 8.8 |
| Model + Curcuma extract | 106.4 | 4.9 | 373.6 | 4.9 |
| Model + Glutamine | 111.3 | 5.3 | 368.8 | 5.3 |
| Model + Curcuma extract + Glutamine | 117.9 | 6.1 | 362.1 | 6.1 |
| Model + *Lactobacillus rhamnosus* GG + Glutamine | 123.9 | 5.7 | 356.1 | 5.7 |
| Model + Curcuma extract + *Lactobacillus rhamnosus* GG | 122.3 | 6.4 | 357.8 | 6.4 |
| Model + Curcuma extract + *Lactobacillus rhamnosus* GG + Glutamine | 121.8 | 4.3 | 358.3 | 4.3 |
| Model + Clomipramine (10 mg/kg) by intraperitoneal injection | 127.4 | 7.1 | 352.6 | 7.1 |

Depression 24 hours after the "elevated maze" test, the depressive behavior is evaluated by means of the tail suspension test.

Figure 3:
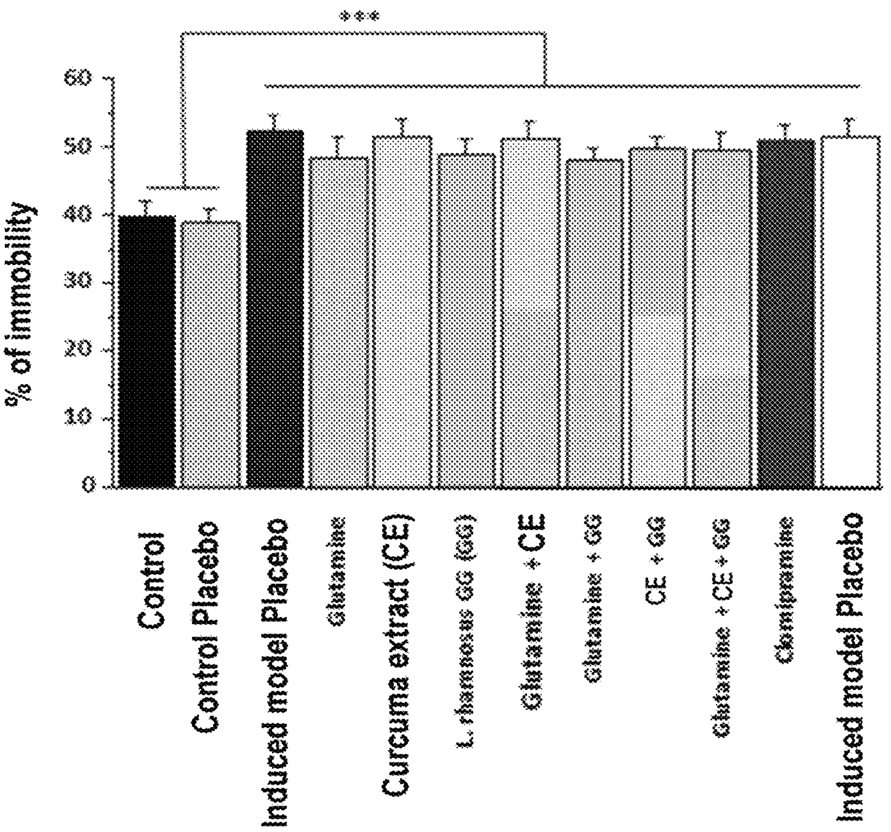
FIG. 3 represents the percentage of immobility during the tail suspension test. The results are the means±standard deviation. *** $p<0.001$ vs "control" and "control+placebo".

FIG. 3 describes the percentage of immobile time for the control animals and the stressed animals.

TABLE 4

Table 4: Results of the tail suspension test The results are the means ± standard deviation. SEM = Standard Error of Mean

| Tail suspension test Group (n = 12) | Mean (seconds) | SEM |
|---|---|---|
| Control | 118.8 | 7.5 |
| Control + Placebo | 116.8 | 6.2 |
| Model + Placebo | 157.3 | 6.4 |

TABLE 4-continued

Table 4: Results of the tail suspension test The results are the means ± standard deviation. SEM = Standard Error of Mean

| Tail suspension test Group (n = 12) | Mean (seconds) | SEM |
|---|---|---|
| Model + *L. rhamnosus* GG | 146.8 | 6.9 |
| Model + Curcuma extract | 154.8 | 7.6 |
| Model + Glutamine | 145.5 | 9.4 |
| Model + Curcuma extract + Glutamine | 154.2 | 7.1 |
| Model + *Lactobacillus rhamnosus* GG + Glutamine | 143.9 | 5.3 |
| Model + Curcuma extract + *Lactobacillus rhamnosus* GG | 149.1 | 5.6 |
| Model + Curcuma extract + *Lactobacillus rhamnosus* GG + Glutamine | 148.1 | 8.1 |
| Model + Clomipramine (10 mg/kg) by intraperitoneal injection | 154.4 | 8.0 |

It is demonstrated that the stressed animals spend a significantly longer time immobile when compared with the control animals (p<0.001).

Conclusion

These results as a whole indicate that 4 weeks of exposure to unpredictable stresses (UCMS) brought about a high state of anxiety and depression in the 6-month-old mice. Even more importantly, all the groups evaluated in the course of phase 2 displayed similar levels of anxiety and of depressive behavior before the administration of the ingredients alone or in combination.

Evaluation of the Formulation and of its Ingredients Alone or in Combination

Anxiety

The anxiety behavior was evaluated by means of the open field test. The mean time spent by the mice at the center of the apparatus is measured.

Figure 4:
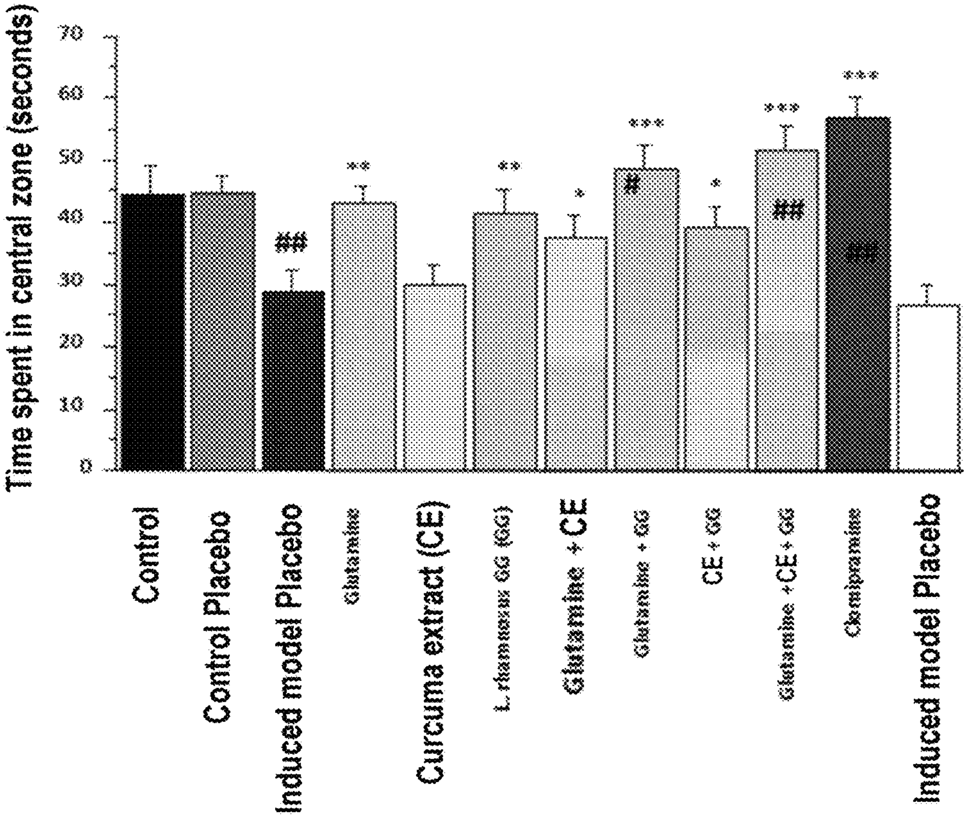
FIG. 4 represents the performance of the open field test on 6-month-old stressed mice after 3 weeks of treatment compared with stressed mice treated with placebo or unstressed mice. The results are the means±standard deviation. * represents a significant difference in comparison with the model/placebo group: * $p<0.05$;  $p<0.01$; * $p<0.001$; #represents a significant difference in comparison with the control/placebo group: #: $p<0.05$ and ##: $p<0.01$.

FIG. 4 shows the effects of the various combinations in comparison with unstressed control groups and with the and with the "model of anxiety and placebo" group, known as the placebo induced model group.

TABLE 5

Table 5. Results of the "Open field" test

| Open field test Group (n = 12) | Mean (seconds) | SEM |
|---|---|---|
| Control | 44.3 | 5 |
| Control + Placebo | 44.7 | 2.8 |
| Model + Placebo | 28.8 | 3.7 |
| Model + *L. rhamnosus* GG | 41.6 | 3.6 |
| Model + Curcuma extract | 29.8 | 3.3 |
| Model + Glutamine | 42.9 | 3 |
| Model + Curcuma extract + Glutamine | 37.7 | 3.4 |
| Model + *Lactobacillus rhamnosus* GG + Glutamine | 48.5 | 3.8 |
| Model + Curcuma extract + Lactobacillus rhamnosus GG | 39.3 | 3.5 |
| Model + Curcuma extract + *Lactobacillus rhamnosus* GG + Glutamine | 51.7 | 3.6 |
| Model + Clomipramine (10 mg/kg) by intraperitoneal injection | 56.8 | 3.4 |

Depression

Figure 5:
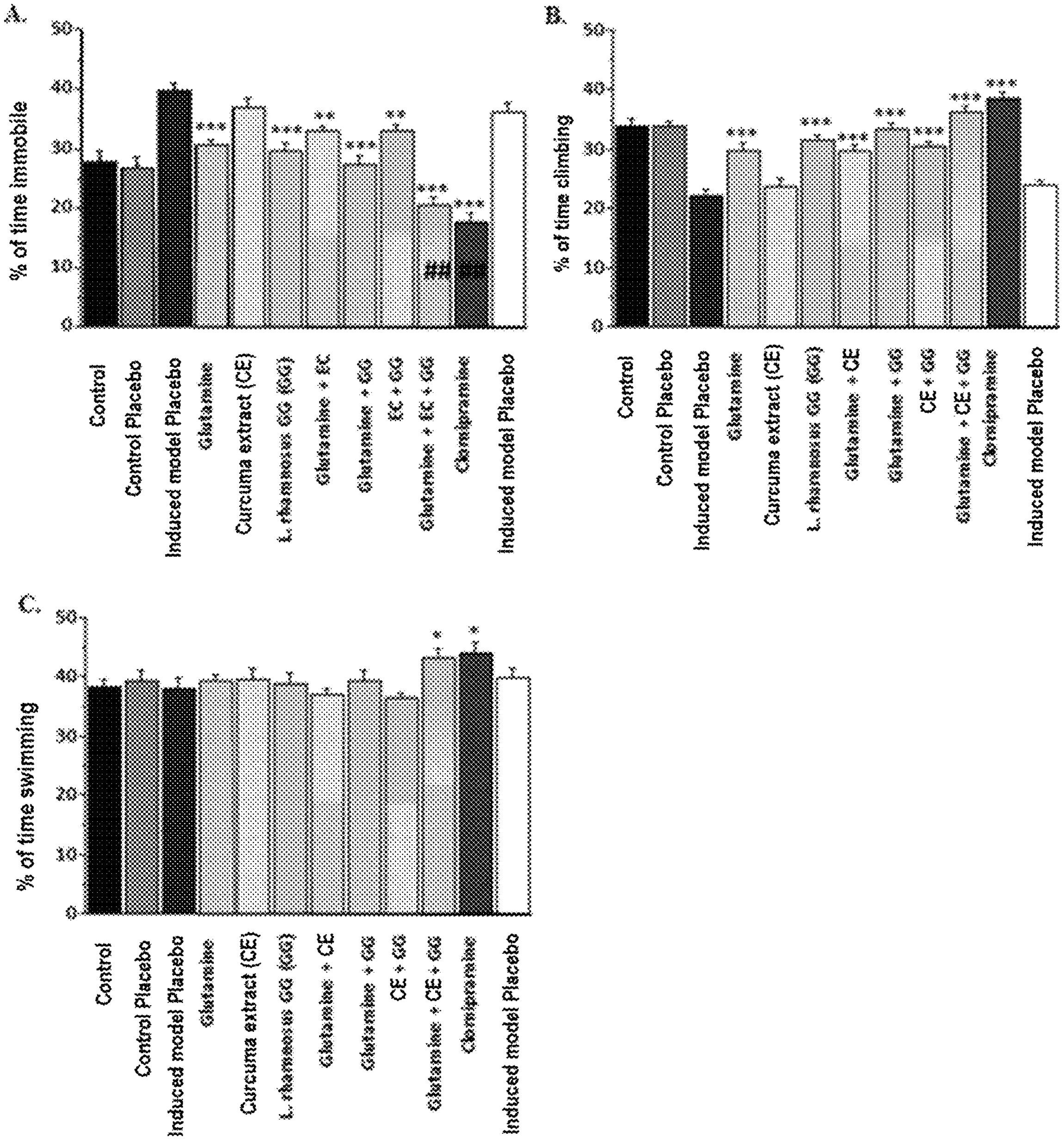
FIG. 5 represents the performance of the forced swim test on 6-month-old stressed mice after 3 weeks of treatment compared with stressed mice treated with placebo or unstressed mice. A-Percentage of immobility time; B-Percentage of climbing time; C-Percentage of swimming time. The results are the means=standard deviation. * represents a significant difference in comparison with the model/placebo group: * $p<0.05$;  $p<0.01$; * $p<0.001$; #represents a significant difference in comparison with the control/placebo group: #: $p<0.05$ and ##: $p<0.01$

Immobility Time (FIG. 5A and Table 6):

The one-way ANOVA statistical analysis demonstrates a significant difference between the groups, the various treatments not inducing the same effects on the depression and anxiety symptoms (F(11,132)=20.735; p<0.001).

In comparison with the "Model+Placebo group", the post hoc analyses demonstrate that all the treatments except for curcumin (p=0.14) reduce the immobility time to the point of normalizing its level to that of the unstressed animals (p<0.001 for all). Furthermore, it is seen that the Glutamine+*Curcuma*+*Lactobacillus rhamnosus* GG treatment is significantly more effective than these three ingredients tested alone or combined in pairs (p<0.001 for all the groups) and are comparable to the drug treatment by intraperitoneal injection (p=0.13). Finally, the "Glutamine+*Curcuma*+*Lactobacillus rhamnosus* GG" groups reduce the immobility time significantly when compared with the unstressed and untreated animals (p<0.001) and in a manner comparable to that of the "Clomipramine" group.

Climbing Time (FIG. 5B and Table 6):

The one-way ANOVA statistical analysis reveals a significant difference between the groups (F(11,132)=26.504; p<0.001). In comparison with the "Model+Placebo group", the post hoc analyses demonstrate that all the treatments except for curcumin (p=0.25) increase the time spent climbing in the case of the stressed mice.

Furthermore, it is seen that the Glutamine+*Curcuma*+*Lactobacillus rhamnosus* GG treatment is significantly more effective than these three ingredients tested alone or combined in pairs (p<0.001 for all the groups) and are comparable to the drug treatment by intraperitoneal injection (p=0.11).

Swimming Time (FIG. 5C and Table 6):

Finally, the one-way ANOVA statistical analysis reveals a significant difference between the groups (F(11,132)=1.922; p=0.004), the "Glutamine+*Curcuma*+*Lactobacillus rhamnosus* GG" and "clomipramine" groups spending more time swimming when compared with the other groups.

Composition of the Microbiota by Analysis of the 16S rRNA

The composition of the microbiota of the animals was analyzed in order to determine the influence of the formula on the bacterial composition of the fecal microbiota of the stressed mice and to compare it with the influence of the drug or of the placebo.

The animals' feces were sampled in order for a DNA extraction to be performed (Zymo Research based kits). The V3-V4 regions of the 16S rRNA gene are amplified and sequencing is performed on an ILLUMINA MiSeq system using the 2*250 bp mode. Sequence analysis is performed after correction using SPAdes (Bak et al., J. Neurochem. 2006; 98(3): 641-53) and regrouping is performed using PEAR (Zhang J. et al. Bioinformatics 2014; 30(5): 614-20). The OTUs (Operational Taxonomic Units) are identified with the Vsearch tool (Rognes T. et al. Peer J., 2016; 4: e2584), the taxonomic classification arising therefrom was performed by means of the RDP (Ribosomal Database Project) database.

The majority of the diversity studies based on 16S rDNA define the OTUs as being sets of sequences having at least 97% identity with each other. The OTUs are, in point of fact, the unit for measuring the specific richness in microbial ecology.

Statistics

The statistical analyses were performed using the R program (Team RDC. R: A Language and Environment for Statistical Computing. 2012, Austria: R Foundation for Statistical Computing) and various packets (Ade4, Vegan). The Wilcoxon or Kruskal-Wallis post-tests were used to compare the groups. The Wilcoxon paired tests were used for the paired comparisons between the groups, with corrections for the multiple tests. Several tests were corrected by means of the false discovery rate method (q-value).

Analysis and Results

A total of 3824 OTUs was obtained with a mean of 1312±159 OTUs detected per sample.

Figure 6:
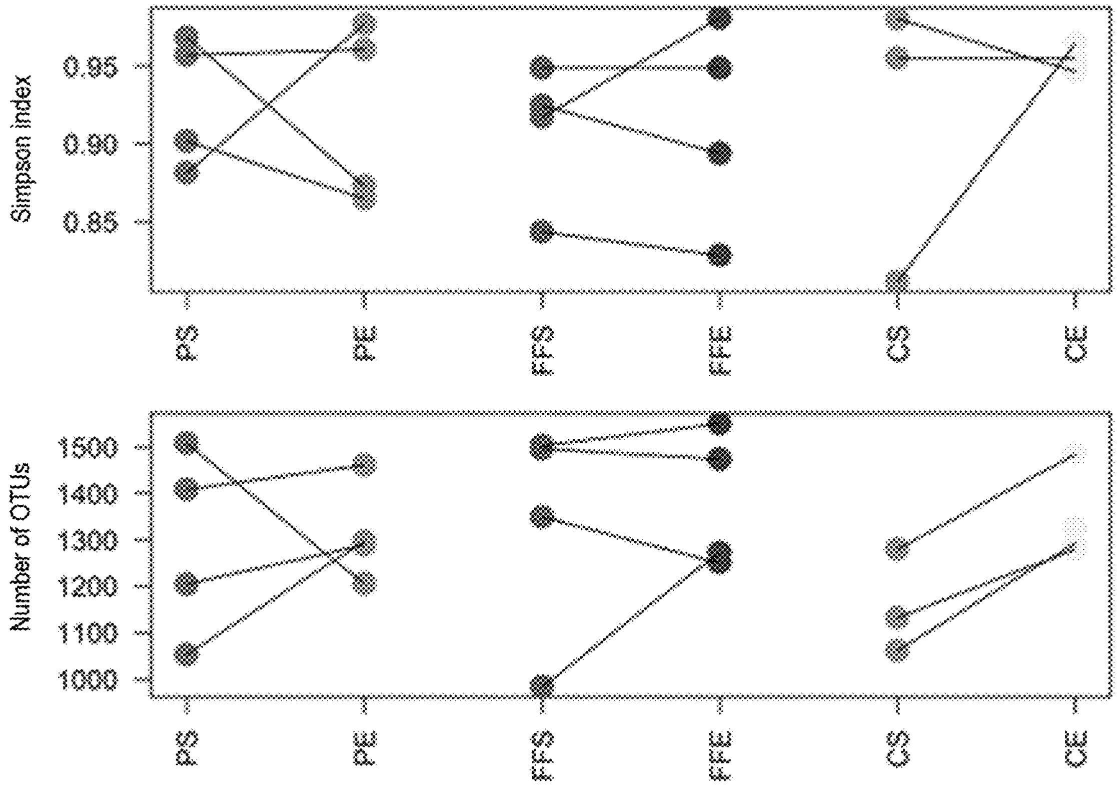
FIG. 6 represents the microbial diversity. PS=Placebo group/Start (before treatment); PE=Placebo group/End (after treatment); FFS=Full formulation/Start; FFE=Full formulation/End; CS=Clomipramine group/Start; CE=Clomipramine group/End.

No significant difference was revealed between the groups before or after treatment. The microbial diversity (α-diversity) is virtually identical from one sample to another (FIG. 6).

Figure 8:
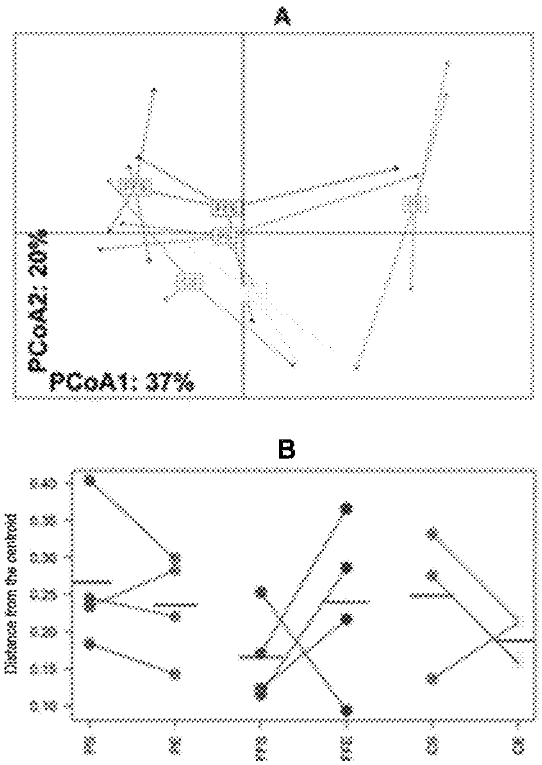
FIG. 8 represents A—The beta-diversity (β) of the intestinal microbiota evaluated by principal component analysis (PCoA). The PCoA was calculated on the genera using the Bray-Curtis dissimilarity matrix. The first two components are displayed and summarize 57% of the data inertia. B—Band diagram illustrating the distances between the samples and the profile of the centroid microbiota of each group of mice.

As shown in FIG. 8—A and according to the PCoA1 axis, the placebo group has the microbiotal profile which changed the most relative to the other groups (complete formula and clomipramine). This means that the treatments (complete formula and clomipramine) would stabilize the dysbiosis induced by the 4 weeks of stress relative to the placebo group whose intestinal ecosystem continues to drift.

In conclusion this study showed that 4 weeks of UCMS induced anxiety and depressive symptoms in 6-month-old mice, in comparison with unstressed mice. Furthermore, the stressed mice always showed an increase in anxiety and depressive behaviour 28 days after stopping the UCMS procedure, which indicates a severe and long-term resistant increase in the reactivity to fear. It is demonstrated herein that all the chronic treatments, with the exception of the curcuma extract administered alone, decreased the anxiety and the depressive symptoms.

Furthermore, it was observed that the chronic treatment with the glutamine+curcuma+*Lactobacillus rhamnosus* GG combination is the most efficient combination for i) restoring a normal level of emotional reactivity, as powerful as clomipramine, relative to the stressed group+placebo, ii) significantly reducing the reactivity to fear and the depressive behavior relative to the unstressed controls, iii) modulating the microbiotal composition relative to the placebo group (stabilization of stress-induced dysbiosis).

Thus, the combination of glutamine+curcuma+*Lactobacillus rhamnosus* GG induced a microbiotal effect combined with an anxiolytic and antidepressant effect. These effects are comparable to those obtained with clomipramine.

The combination according to the invention thus makes it possible after 21 days of treatment to potentiate the effect relative to the ingredients alone or combined in pairs. This combination makes it possible after 21 days of treatment to obtain an effect that is comparable to that of clomipramine administered intraperitoneally.

TABLE 6

Results of the forced swim test. A - Percentage of immobility time; B - Percentage of climbing time; C - Percentage of swimming time. The results are the means ± standard deviation.

| Group (n = 12) | Immobility (dry) | SEM | Climbing (dry) | SEM | Swimming (dry) | SEM |
|---|---|---|---|---|---|---|
| Control | 100.3* | 6.7 | 122.0 | 4.2 | 137.7 | 4.9 |
| Control + Placebo | 96.3* | 7.3 | 121.9 | 2.8 | 141.8 | 6.8 |
| Model + Placebo | 143.4* | 4.9 | 79.3* | 3.8 | 137.3 | 6.4 |
| Model + *Lactobacillus rhamnosus* GG | 106.8* | 5.0 | 113.5* | 2.5 | 139.8 | 6.9 |
| Model + Curcuma extract | 132.8* | 5.8 | 85.1* | 4.6 | 142.2 | 6.5 |
| Model + Glutamine | 111.0* | 2.9 | 107.3* | 3.9 | 141.8 | 3.6 |
| Model + Curcuma extract + Glutamine | 119.4* | 2.4 | 107.3* | 3.7 | 133.3 | 3.7 |
| Model + *Lactobacillus rhamnosus* GG + Glutamine | 98.5* | 5.6 | 119.8* | 3.8 | 141.8 | 6.5 |
| Model + Curcuma extract + *Lactobacillus rhamnosus* GG | 119.3* | 3.3 | 109.9* | 2.3 | 130.8 | 3.2 |
| Model + Curcuma extract + *Lactobacillus rhamnosus* GG + Glutamine | 74.5 | 4.5 | 130.3 | 4.2 | 155.3 | 5.6 |
| Model + Clomipramine (10 mg/kg) by intraperitoneal injection | 63.6 | 5.3 | 138.3 | 3.8 | 158.1 | 6.6 |

Figure 7:
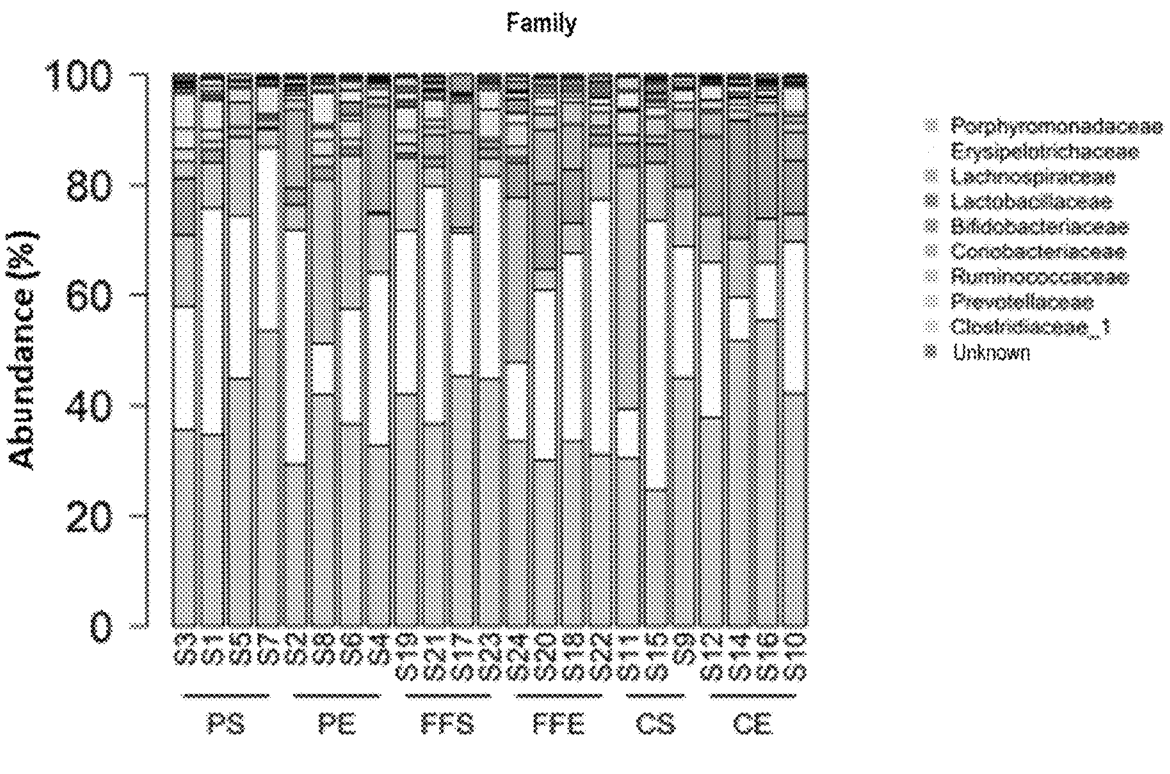
FIG. 7 represents the composition of the intestinal microbiota (distribution as a percentage per family). PS=Placebo group/Start (before treatment); PE=Placebo group/End (after treatment); FFS=Full formulation/Start; FFE=Full formulation/End; CS=Clomipramine group/Start; CE=Clomipramine group/End.

The composition of the microbiota showed a similar distribution of the bacterial families between the samples, the Porphyromonadaceae (39±8%) and the Erysipelotrichaceae (28±12%) being the most abundant bacterial families (FIG. 7).

Table 6: Results of the Forced Swim Test. A—Percentage of Immobility Time; B—Percentage of Climbing Time; C—Percentage of Swimming Time. The Results are the Means±Standard Deviation.

Examples of Formulation of the Composition

TABLE 7

| Example 1 | Stick-packs mg | % |
|---|---|---|
| Glutamine | 2000 | 90.29 |
| Curcuma extract | 100 | 4.51 |
| *Lactobacillus rhamnosus* GG | 10 | 0.45 |
| Maltodextrin | 100 | 4.51 |
| Silicon dioxide | 5 | 0.22 |
| TOTAL | 2215 | 100 |

| Example 2 | mg per one gel capsule | % |
|---|---|---|
| Glutamine | 500 | 76.92 |
| Curcuma extract | 50 | 7.69 |
| *Lactobacillus rhamnosus* GG | 20 | 3.07 |
| Maltodextrin | 75 | 11.53 |
| Magnesium stearate | 5 | 0.76 |
| TOTAL | 650 | 100 |

| Example 3 | mg per two gel capsules | % |
|---|---|---|
| Glutamine | 1000 | 86.02 |
| Curcuma extract | 50 | 4.3 |
| *Lactobacillus rhamnosus* GG | 10 | 0.86 |
| Maltodextrin | 100 | 8.6 |
| Magnesium stearate | 2.5 | 0.21 |
| TOTAL | 1162.5 | 100 |

The invention claimed is:

1. A pharmaceutical, nutraceutical or food product comprising a composition consisting of glutamine, a *Curcuma* extract and *Lactobacillus rhamnosus*, characterized in that the glutamine, the *Curcuma* extract and the *Lactobacillus rhamnosus* are present in the composition in the following proportions:

from 90 to 96% by weight of glutamine, from 3% to 6% by weight of *Curcuma* extract, from 0.25% to 5% by weight of *Lactobacillus rhamnosus*, per 100% by weight of the sum of glutamine, *Curcuma* extract and *Lactobacillus rhamnosus*, wherein the *Curcuma* extract comprises at least 15% of curcuminoids and the *Curcuma* extract is encapsulated in a cyclodextrin.

2. The composition as claimed in claim 1, in which the *Lactobacillus rhamnosus* strain is the strain *Lactobacillus rhamnosus* GG.

3. The composition as claimed in claim 1, in which the *Lactobacillus rhamnosus* bacteria are in live form.

4. The composition as claimed in claim 1, further comprising:

one or more prebiotics; and/or vitamins, minerals and/or trace elements; and/or powders or extracts of plants, fruit, vegetables, algae or fungi; and one or more probiotics selected from the group consisting of bacteria of the genera Enterobactericeae, *Enterococcus, Faecalibacterium, Fusobacterium, Odoribacter*, Parabacterides, *Pediococcus, Roseburia, Ruminococcus* and *Streptococcus* and/or yeasts of the genus *Saccharomyces*.

5. A method of treating an emotional disorder in an individual in need thereof, the method comprising administering a composition according to claim 1 to the individual.

6. The method as claimed in claim 5, in which the emotional disorder is an anxiety disorder and/or a mood disorder.

7. The method as claimed in claim 6, in which the emotional disorder is depression or anxiety.

8. The method as claimed in claim 5, wherein the composition is in a form for oral or enteral administration.

9. The method as claimed in claim 5, characterized in that the composition is in a form suitable for a daily administration of between 0.5 and 10 g of glutamine, between 25 mg and 500 mg of *Curcuma* extract and between 0.05 mg and 500 mg of *Lactobacillus rhamnosus*.

10. The composition of claim 1, said composition being in the form of dose units, each dose unit comprising: glutamine between 0.5 and 10 g, the *Curcuma* extract between 25 mg and 500 mg and *Lactobacillus rhamnosus* between 0.05 mg and 500 mg.

11. The composition of claim 1, wherein the *Curcuma* extract is a *Curcuma longa* extract.

12. The composition of claim 1, wherein the cyclodextrin is a gamma-cyclodextrin.

13. The composition of claim 10, wherein the dose units are in the form of powders, tablets or gel capsules.

* * * * *